US009133504B2

(12) United States Patent
Hassibi et al.

(10) Patent No.: US 9,133,504 B2
(45) Date of Patent: Sep. 15, 2015

(54) REAL TIME MICROARRAYS

(75) Inventors: Arjang Hassibi, Austin, TX (US);
Babak Hassibi, San Marino, CA (US);
Haris Vikalo, Pasadena, CA (US); Jose Luis Riechmann, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/758,621

(22) Filed: Jun. 5, 2007

(65) Prior Publication Data

US 2008/0039339 A1 Feb. 14, 2008

Related U.S. Application Data

(60) Provisional application No. 60/811,064, filed on Jun. 5, 2006, provisional application No. 60/840,060, filed on Aug. 24, 2006.

(51) Int. Cl.
*C12Q 1/68* (2006.01)

(52) U.S. Cl.
CPC ............ *C12Q 1/6818* (2013.01); *C12Q 1/6837* (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 4,562,157 A | 12/1985 | Lowe et al. | |
| 4,711,955 A | 12/1987 | Ward et al. | |
| 4,994,373 A | 2/1991 | Stavrianopoulos et al. | |
| 5,034,506 A | 7/1991 | Summerton et al. | |
| 5,082,830 A | 1/1992 | Brakel et al. | |
| 5,216,141 A | 6/1993 | Benner | |
| 5,235,033 A | 8/1993 | Summerton et al. | |
| 5,328,824 A | 7/1994 | Ward et al. | |
| 5,386,023 A | 1/1995 | Sanghvi et al. | |
| 5,449,767 A | 9/1995 | Ward et al. | |
| 5,476,928 A | 12/1995 | Ward et al. | |
| 5,491,063 A | 2/1996 | Fisher et al. | |
| 5,571,673 A | 11/1996 | Picone | |
| 5,573,906 A | 11/1996 | Bannwarth et al. | |
| 5,599,668 A * | 2/1997 | Stimpson et al. ................ | 435/6 |
| 5,602,240 A | 2/1997 | De Mesmaeker et al. | |
| 5,632,957 A | 5/1997 | Heller et al. | |
| 5,637,684 A | 6/1997 | Cook et al. | |
| 5,644,048 A | 7/1997 | Yau | |
| 5,656,493 A | 8/1997 | Mullis et al. | |
| 5,744,305 A | 4/1998 | Fodor et al. | |
| 5,807,522 A | 9/1998 | Brown et al. | |
| 5,871,928 A | 2/1999 | Fodor et al. | |
| 5,974,164 A | 10/1999 | Chee | |
| 6,025,601 A | 2/2000 | Trulson et al. | |
| 6,040,193 A | 3/2000 | Winkler et al. | |
| 6,048,690 A | 4/2000 | Heller et al. | |
| 6,054,270 A | 4/2000 | Southern | |
| 6,083,763 A | 7/2000 | Balch | |
| 6,110,426 A | 8/2000 | Shalon et al. | |
| 6,124,102 A | 9/2000 | Fodor et al. | |
| 6,174,670 B1 | 1/2001 | Wittwer et al. | |
| 6,225,625 B1 | 5/2001 | Pirrung et al. | |
| 6,261,776 B1 | 7/2001 | Pirrung et al. | |
| 6,291,183 B1 | 9/2001 | Pirrung et al. | |
| 6,319,958 B1 | 11/2001 | Johnson et al. | |
| 6,465,175 B2 | 10/2002 | Horn et al. | |
| 6,600,996 B2 | 7/2003 | Webster et al. | |
| 6,610,482 B1 | 8/2003 | Fodor et al. | |
| 6,673,536 B1 * | 1/2004 | Stoughton et al. ........... | 435/6.14 |
| 6,750,963 B2 | 6/2004 | Sampas | |
| 6,814,934 B1 | 11/2004 | Higuchi | |
| 7,064,197 B1 | 6/2006 | Rabbani et al. | |
| 7,361,472 B2 * | 4/2008 | Yguerabide et al. ........... | 435/7.1 |
| 2002/0001844 A1 * | 1/2002 | Frutos et al. ...................... | 436/6 |
| 2002/0106653 A1 | 8/2002 | Kurane et al. | |
| 2002/0150917 A1 | 10/2002 | Weidenhammer et al. | |
| 2003/0143591 A1 | 7/2003 | Davies et al. | |
| 2004/0147045 A1 | 7/2004 | Nelson | |
| 2005/0065290 A1 | 3/2005 | Shah | |
| 2005/0112585 A1 | 5/2005 | Zichi et al. | |
| 2006/0068378 A1 | 3/2006 | Mirkin et al. | |
| 2006/0078929 A1 | 4/2006 | Bickel et al. | |
| 2007/0026421 A1 | 2/2007 | Sundberg et al. | |

(Continued)

FOREIGN PATENT DOCUMENTS

EP 0236069 B1 5/1997
WO WO 00/79009 A2 12/2000

(Continued)

OTHER PUBLICATIONS

Campbell, et al. Large-scale approaches for glycobiology. Genome Biology. 2005; 6(11): 236.1-8.
Feng, L. Probing lipid-protein interactions using lipid microarrays. Prostaglandins Other Lipid Mediat. 2005; 77(1-4):158-67.
Gunderson, et al.—Decoding Randomly Ordered DNA Arrays. Genome Res. 2004; 14:870-877.
Han, et al. Quantum-dot-tagged microbeads for multiplexed optical coding of biomolecules.Nature Biotechnology. 2001; 19, 631-635.

(Continued)

*Primary Examiner* — Christopher M Gross
(74) *Attorney, Agent, or Firm* — Wilson Sonsini Goodrich & Rosati

(57) ABSTRACT

This invention provides methods and systems for measuring the binding of analytes in solution to probes bound to surfaces in real-time. The method involves contacting a fluid volume having a plurality of different analytes with a solid substrate having a plurality of different probes. The probes are capable of specifically binding to the analytes. The method also involves measuring signals at multiple time points while the fluid volume is in contact with the substrate. The signals measured at multiple time points can be correlated with the amount of binding of the analytes with the probes. The method eliminates the need to wash the probes before measuring the binding characteristics.

10 Claims, 19 Drawing Sheets

(56) References Cited

U.S. PATENT DOCUMENTS

| | | | |
|---|---|---|---|
| 2007/0065818 | A1 | 3/2007 | Foti et al. |
| 2007/0077609 | A1 | 4/2007 | Gambhir et al. |
| 2014/0363821 | A1 | 12/2014 | Bashir et al. |

FOREIGN PATENT DOCUMENTS

| | | | |
|---|---|---|---|
| WO | WO 01/86001 A1 | 11/2001 | |
| WO | WO 00/79009 A3 | 1/2002 | |
| WO | WO 02/30946 A1 | 4/2002 | |
| WO | WO 02/099397 A2 | 12/2002 | |
| WO | WO 03/062791 A2 | 7/2003 | |
| WO | WO 2004/011144 A2 | 2/2004 | |
| WO | WO 03/062791 A3 | 6/2004 | |
| WO | WO 2004/059006 A1 | 7/2004 | |
| WO | WO 2005/118870 A2 | 12/2005 | |
| WO | WO 2005/121159 A1 | 12/2005 | |
| WO | WO 2006/014351 A2 | 2/2006 | |
| WO | WO 2006/037527 A1 | 4/2006 | |
| WO | WO 2006/053769 A1 | 5/2006 | |

OTHER PUBLICATIONS

Hassibi, et al. A probabilistic model for inherent noise and systematic errors of microarrays. Proc of Workshop on Genomics Signal Processing and Statistics. 2005: 1-2.

Hassibi, et al. A stochastic model and simulation algorithm for polymerase chain reaction (PCR) systems. Proc of Workshop on Genomics Signal Processing and Statistics. 2004: 1-4.

Hassibi, et al. Biological shot-noise and quantum-limited signal-to-noise ratio in affinity-based biosensors. J Appl Phys. 2005; 97: 084701.1-10.

Hauss. Electromagnetic nose and quantum optical measurements. Springer. NY 2000. Chap. 4. p. 127.

Lockhart, et al. Multiplex metallica. Nat Biotechnol. 2001; 19(12):1122-3.

Michael, et al. Randomly Ordered Addressable High-Density Optical Sensor Arrays. Anal. Chem., 1998; 70(7): 1242-1248.

Petersson, et al. A review of the parameter estimation problem of fitting positive exponential sums to empirical data. Technical Report IMa-TOM-1997-08, Department of Mathematics and Physics. Malardalen University, Sweden. 1997: 1-29.

Stolovitzky, et al. Efficiency of DNA replication in the polymerase chain reaction. Proc Natl Acad Sci USA. 1996; 93: 12947-52.

Tu, et al. Quantitative noise analysis for gene expression microarray experiments. Proc Natl Acad Sci USA. 2002; 99: 14031-6.

Vikalo, et al. A statistical model for microarrays, optimal estimation algorithms, and limits of performance. IEEE transactions on signal processing. 2006; 54(6): 2444-2455.

Wang, et al. Estimation of the mutation rate during error-prone polymerase chain reaction. J Comput Biol. 2000; 7(1-2): 143-58.

Zhu, et al. Protein chip technology. Current Opinion in Chemical Biology. 2003; 7: 55-63.

Canon. High resolution thermal melt analysis. http://culs.canon.com/Science/Technology_Overview/High_Resolution_thermal_melt_analysis/High_Resolution_Thermal_Melt_Analysis.shtml. Accessed on Jun. 10, 2015. 1 pg.

Dolganov, et al. Novel molecular diagnostic (MDx) Platform for Highly-Multiplex Drug Susceptibility Testing of M. tuberculosis. http://www.stoptb.org/wg/new_diagnostics/assets/documents/09-NDWG-Annual-Meeting_GarySCHOOLNIK_&_Gregory_DOLGANOV.pdf. Accessed on Jun. 10, 2015. 13 pgs.

Falconnet, et al. Rapid, sensitive and real-time multiplexing platform for the analysis of protein and nucleic-acid biomarkers. Anal Chem. Feb. 3, 2015;87(3):1582-9. doi: 10.1021/ac502741c. Epub Jan. 21, 2015.

Hassibi. CMOS Biochips for Point-of-Care Molecular Diagnostics. Hot Chips—Aug. 2014. 32 pgs.

Nanogen. A chip-based genetic detector for rapid identification of individuals. National institute of justice—Project No. 97-LB-VX-0004. Apr. 2006. 102 pgs.

Salm, et al. Ultralocalized thermal reactions in subnanoliter droplets-in-air. Proc Natl Acad Sci U S A. Feb. 26, 2013;110(9):3310-5. doi: 10.1073/pnas.1219639110. Epub Feb. 11, 2013.

Savyon Diagnostics. Nano CHIP. www.nanochip400.com. NG Jun. 2010—VER1. 8pgs.

Scherf, et al. Letter from Uwe Scherf-S to Kristen Kanack re: K143178 Section 510(k). Department of Health & Human Services. Jan. 30, 2015. 9pgs.

Hassibi, et al. Real-time DNA microarray analysis. Nucleic Acids Res. Nov. 2009;37(20):e132. doi: 10.1093/nar/gkp675. Epub Aug. 31, 2009.

International search report and opinion dated Mar. 3, 2008 for PCT/US2007/0070449.

European search report and search opinion dated Aug. 4, 2009 for EP Application No. 07784330.8.

European search report and search opinion dated Nov. 5, 2012 for EP Application No. 12161041.4.

Ausubel, et al. Current Protocols in Molecular Biology. Eds., Greene Pub. Associates and Wiley Interscience, 1987.

Beaucage, et al. The functionalization of oligonucleotides via phosphoramidite derivatives. Tetrahedron 49.10 (1993): 1925-1963.

Borrebaeck. Antibody Engineering. 2nd edition, Ed., Oxford University Press, New York, 1995.

Brill, et al. Synthesis of oligodeoxynucleoside phosphorodithioates via thioamidites. Journal of the American Chemical Society, 1989, 111(6), 2321-2322.

Carlsson, et al. Screening for genetic mutations. Nature. Mar. 21, 1996;380(6571):207.

Clegg. Fluorescence resonance energy transfer and nucleic acids. Methods Enzymol. 1992;211:353-88.

Cronin, et al. Cystic fibrosis mutation detection by hybridization to light-generated DNA probe arrays. Hum Mutat. 1996;7(3):244-55.

De Mesmaeker, et al. Comparison of rigid and flexible backbones in antisense oligonucleotides. Bioorganic & Medicinal Chemistry Letters, 1994 4(3), 395-398.

Denpcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.

Diamandis, et al. Immunoassay. Eds., Academic Press, Inc., San Diego, 1996.

Eckstein. Oligonucleotides and Analogues: A Practical Approach. Press at Oxford University Press, 1991: 313.

Forster. Experimentelle und theoretische Untersuchung des zwischenmolekularen Übergangs von Elektronenanregungsenergie. Zeitschrift für naturforschung A 4.5 1949: 321-327.

Gao, et al. Unusual Conformation of a 3'-thioformacetal Linkage in a DNA Duplex. Journal of biomolecular NMR, 1994, 4(1), 17-34.

Hall. Biosensors. Prentice Hall. 1991. Englewood Cliffs, NJ. (Table of contents only).

Hassibi, et al. A Programmable 0.18-um CMOS Electrochemical Sensor Microarray for Biomolecular Detection. Sensors Journal, IEEE,Dec. 2006vol. 6, Issue: 6: 1380-1388.

Hassibi. Integrated Microarrays. Ph.D. Thesis Stanford University, 2005.

Herzenberg, et al. Handbook of Experimental Immunology. Eds, Blackwell Science, Cambridge, Mass., 1996.

Horn, et al. Oligonucleotides with alternating anionic and cationic phosphoramidate linkages: synthesis and hybridization of stereo-uniform isomers. Tetrahedron letters,1996, 37(6), 743-746.

Jenkins, et al.The biosynthesis of carbocyclic nucleosides. Chem. Soc. Rev., 1995, 24(3), 169-176.

Jepsen, et al. Locked nucleic acid: a potent nucleic acid analog in therapeutics and biotechnology. Oligonucleotides. 2004;14(2):130-46.

Johnstone, et al. Immunochemistry in practice. Oxford: Blackwell science, 1996.

Khabzaoui, et al. A multicriteria genetic algorithm to analyze microarray data. In Evolutionary Computation, Jun. 2004. CEC2004. Congress on vol. 2, pp. 1874-1881. IEEE.

Kiedrowski, et al. Parabolic Growth of a Self-Replicating Hexadeoxynucleotide Bearing a 3'-5'-Phosphoamidate Linkage. Angewandte Chemie International Edition in English, 1991, 30(4), 423-426.

(56) References Cited

OTHER PUBLICATIONS

Letsinger, et al. Cationic oligonucleotides. Journal of the American Chemical Society, 1988 110(13), 4470-4471.

Letsinger, et al. Hybridization of alternating cationic/anionic oligonucleotides to RNA segments. Nucleosides, Nucleotides & Nucleic Acids 13.6-7 (1994): 1597-1605.

Metzker. Sequencing technologies—the next generation. Nat Rev Genet. Jan. 2010;11(1):31-46. doi: 10.1038/nrg2626. Epub Dec. 8, 2009.

Petersson, et al. Applied Mathematics and Computation. Feb. 2002. vol. 126: No. 1. 31-61.

Pourmand, et al. Direct electrical detection of DNA synthesis. Proc Natl Acad Sci U S A. Apr. 25, 2006;103(17):6466-70. Epub Apr. 13, 2006.

Rehmna, et al. Immobilization of acrylamide-modified oligonucleotides by co-polymerization. Nucleic Acids Res. Jan. 15, 1999;27(2):649-55.

Rothe, et al. Multi-target electrochemical biosensing enabled by integrated CMOS electronics. Journal of Micromechanics and Microengineering, 2011, 21(5), 054010.

Sanghvi, et al. Chapters 2 and 3, ASC Symposium Series 580, "Carbohydrate Modifications in Antisense Research", 1994.

Sanghvi, et al. Chapters 6 and 7, ASC Symposium Series 580, "Carbohydrate Modifications in Antisense Research", 1994.

Schena, Protein Microarrays. Jones and Bartlett Publishers. Sudbury, MA. 2005. (Table of contents only).

Schena. Microarray Analysis. Wiley-Liss: A John Wiley & Sons, Inc., Publication. 2003. Hoboken, New Jersey. (Table of contents only).

Schena. Microarray Biochip Technologies. Biotechniques Books. Eaton Pub. Mar. 2000.

Stillman, et al. FAST slides: a novel surface for microarrays. Biotechniques. Sep. 2000;29(3):630-5.

Stimpson, et al. Real-time detection of DNA hybridization and melting on oligonucleotide arrays by using optical wave guides. Proc Natl Acad Sci U S A. Jul. 3, 1995;92(14):6379-83.

Stochastic Matrix, one page, 2013. Wolfram MathWorld. Obtained online on May 29, 2013.

Tijssen. Chapter 3 of Laboratory Techniques in Biochemistry and Molecular Biology: Hybridization with Nucleic Acid Probes, Part I. Theory and Nucleic Acid Preparation. Elsevier, N.Y. 1993.

Van Der Ziel. Noise in solid state devices and circuits. 9th ed. John Wiley & Sons, Inc. 1986. Canada. (Table of contents only).

Vikalo, et al. Optimal estimation of gene expression levels in microarrays. Presented at the IEEE Int. Workshop Genomic Signal Processing Statistics, Newport, RI, May 22-24, 2005.

Vikalo, et al. Proof of publication date of [Vikalo, et al. Optimal estimation of gene expression in microarrays.] as Mar. 5, 2005, one page, acquired from USPTO Library on Jun. 13, 2014.

Yuen, et al. Accuracy and calibration of commercial oligonucleotide and custom cDNA microarrays. Nucleic Acids Res. May 15, 2002;30(10):e48.

Zhang. Noisy Data with Outliers, one page, 1996. Obtained online on Feb. 9, 2013.

* cited by examiner

Figure 11
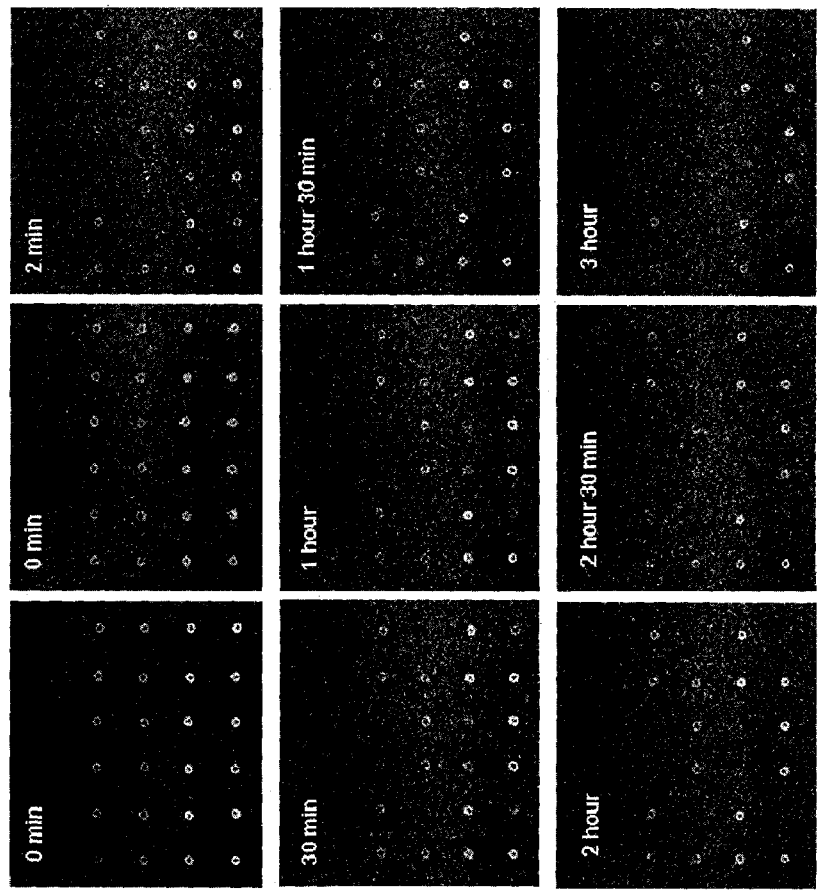
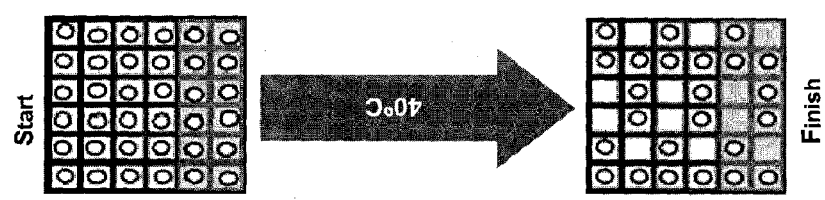

REAL TIME MICROARRAYS

CROSS-REFERENCE

This application claims priority to U.S. Provisional Application Nos. 60/811,064, filed Jun. 5, 2006, and 60/840,060 filed on Aug. 24, 2006, which are incorporated herein by reference in their entirety.

BACKGROUND OF THE INVENTION

Affinity-based biosensors exploit selective binding and interaction of certain bio-molecules (recognition probes) to detect specific target analytes in biological samples. The essential role of the biosensor platforms and the parallel and miniaturized version of them as microarrays are to exploit specific bindings of the probe-target complexes to produce detectable signals, which correlate with the presence of the targets and conceivably their abundance. The essential components of such a system include the molecular recognition layer (capturing probes) integrated within or intimately associated with a signal-generating physiochemical transducer and a readout device.

To generate target-specific signal, the target analytes in the sample volume generally first need to collide with the recognition layer, interact with the probes, bind to the correct probes, and ultimately take part in a transduction process. The analyte motion in typical biosensor settings (e.g., aqueous biological buffers) can be dominated by diffusion spreading, which from a microscopic point of view is a probabilistic mass-transfer process (modeled as a random walk for each analyte molecule). Accordingly, analyte collisions with probes become a stochastic process. Moreover, because of the quantum-mechanical nature of chemical bond forming, the interaction between the probes and the analytes molecules is also probabilistic, thus further contributing to uncertainty and noise corruption of the measured data in biosensors and microarrays. We view such phenomena as inherent noise in the detection system, which results in unavoidable uncertainties even when the measurements are noiseless. Such inherent noise is essentially inevitable since it originates from the stochastic nature of molecular-level interactions. Its examples include Poisson noise sources in microarrays and image sensor detection shot-noise.

Beside the inherent noise, other non-idealities also corrupt the signal obtained by the microarray experiments. Examples of such phenomena include probe density variations, sample preparation systematic errors, and probe saturation. We define systematic errors as the unwanted deviations from the intended detection procedure. If these errors are accurately evaluated, in theory, they can be compensated by post experiment data processing.

Gene expression microarrays are a widely used microarray platform. These systems can measure the expression level of thousands of genes simultaneously, providing a massively-parallel affinity-based detection platform in life science research. Unfortunately, the uncertainty originating from both inherent noise sources and systematic errors in each experiment can obscure some of the important characteristics of the biological processes of interest. The expression level uncertainty (overall measurement error) in microarrays, can originate from the probabilistic characteristics of detection process as mentioned before, all the way from sample extraction and mRNA purification to hybridization and fluorescent intensity measurements. Currently, there are various techniques which attempt to increase the accuracy and signal-to-noise ratio (SNR) of the estimated values. Nonetheless, these techniques often rely on comparative methods, redundant spots, or mathematical algorithms which introduce confidence zones by excluding the unreliable data and outliers. Independent of the method utilized, the degree in which the SNR can be improved in such approaches can still be limited by the inherent microarray noise and systematic errors.

The interfering signals originating from non-specific bindings in microarrays are generally referred to as "background signals." Traditionally in microarray analysis, background signals and their fluctuations are all considered as corruptive noise without any signal content. Users often implement a sub-optimal yet widely adopted approach. This technique defines a confidence threshold level for the signal intensity in view of the background, which effectively divides the signals into irrelevant (below threshold) and relevant (above threshold) regimes. This particular approach is theoretically valid and optimal only when there is a global background signal which is constant everywhere. In practical microarray experiments, this assumption may not be not valid since the background and fluctuation level varies between spots. The approach can thus be sub-optimal. Even when local background subtraction methods are employed, the intensity data are sub-optimally processed, as the background signal that is present in the immediate vicinity of a given microarray probe spot may not actually be the same as the background signal from within the spot. The major outcome of background subtraction, regardless of the method that is used, is that the minimum detectable level (MDL) is higher than necessary. It also contributes more errors in ratio analysis approaches, since low level signals are basically truncated away. Both of these effects in turn can reduce the microarray detection dynamic range.

Beside all the uncertainties within the measurement results, there is also one major question in microarrays and all essentially affinity-based biosensor systems, and that is of the necessary incubation time (hybridization time for DNA microarrays). Since the incubation kinetics in the microarrays experiments is a function of analyte diffusion, reaction chamber size, temperature and binding kinetics of every analyte species, as well as the unknown analyte concentrations, the settling time of the system is quite complex and unpredictable. Although all these questions can, to some extent, be empirically addressed, they are still major impediments in microarray technology and platform-to-platform inconsistencies can be caused by them.

In conventional fluorescent-based microarrays and other extrinsic reporter-based (label-based) biosensors assays, the detection of captured analytes is usually carried out after the incubation step. In some cases, proper fluorescent and reporter intensity measurements are compromised in the presence of a large concentration of floating (unbound) labeled species in the incubation solution, whose signal can overwhelm the target-specific signal from the captured targets. When the incubation is ceased and the solution is removed from the surface of the array, the washing artifacts often occur that make the analysis of the data even more challenging. Thus there exists a need for affinity based sensors that are able to simultaneously obtain high quality measurements of the binding characteristics of multiple analytes, and that are able to determine the amounts of those analytes in solution.

SUMMARY OF THE INVENTION

One aspect of the invention is a method comprising measuring binding of analytes to probes on a microarray in real-time. In one embodiment, the method comprises the steps of:

contacting a fluid volume comprising a plurality of different analytes with a solid substrate comprising a plurality of different probes, wherein the probes are capable of specifically binding with the analytes; and measuring signals at multiple time points while the fluid volume is in contact with the substrate, wherein the signals measured at multiple time points can be correlated with the amount of binding of the analytes with the probes. One embodiment of the method further comprises using the signals measured at multiple time points to determine the concentration of an analyte in the fluid volume. In some embodiments, a change in the signals with time correlates with the amount of the analytes bound to the probes.

In some embodiments, the signals comprise electrochemical, electrical, mechanical, magnetic, acoustic, or electromagnetic signals. In some embodiments, the signals are electromagnetic signals comprising fluorescence, absorption, or luminescence. In some embodiments, the analytes comprise quenching moieties, and the electromagnetic signals measured at multiple time points correlate, at least in part to the quenching of fluorescence. In some embodiments, the fluorescence that is quenched is due at least in part to fluorescent moieties bound to the probes. In some embodiments, the fluorescence that is quenched is due at least in part to fluorescent moieties bound to the solid substrate, wherein such fluorescent moieties are not covalently bound to the probes. In some embodiments, the fluorescence that is quenched is due at least in part to fluorescent moieties that are non-covalently bound to the probe. In some embodiments, the optical signals measured at multiple time points are due, at least in part, to fluorescent resonance energy transfer (FRET).

In some embodiments, the different probes are located on the solid substrate at different addressable locations. In some embodiments there are at least about 3, 4, 5 10, 50, 100, 500, 1000, 10,000, 100,000, or 1,000,000 probes. In some embodiments, the solid substrate comprises one or more beads.

In some embodiments, the analytes and/or the probes comprise the chemical species of nucleic acids or nucleic acid analogs, proteins, carbohydrates, or lipids. In some embodiments, the analytes and the probes are the same type of chemical species. In some embodiments, the analyte and the probe are each a different type of chemical species. In some embodiments, the analyte and the probe comprise nucleic acids or nucleic acid analogs. In some embodiments, the probes comprise proteins, which in some cases can comprise antibodies or enzymes.

In some embodiments, the at least two time points are measured at a time when the amount of binding of an analyte to a probe corresponding to that signal is less than 50% of saturation.

In some embodiments, two or more time points are measured when the fluid volume is at one temperature, and two or more time points are measured when the fluid volume is at a second temperature. In some embodiments, two or more time points are measured when the analyte in the fluid volume is at one concentration, and two or more time points are measured when the fluid volume is at a second concentration. In some embodiments, the concentration of the analyte is enriched between the sets of time points. In some embodiments, the concentration of the analyte is diluted between the sets of time points.

In some embodiments, the solid substrate also comprises control spots.

In some embodiments, the method comprises the use of multiple fluorescent species, with different excitation and/or emission spectra. In some embodiments, the method comprises the use of multiple quencher species, with different quenching properties.

In some embodiments the method further comprises determining binding of a probe with two or more analytes comprising subjecting binding data corresponding to signal and time to an algorithm which determines the contribution of each of the two or more analytes to the binding data. In some embodiments, the probes comprise a fluorescent moiety and the initial surface concentration of probes is determined by measuring fluorescence.

One aspect of the invention is a method of claim 2 wherein: (i) the analytes comprise nucleic acid molecules labeled with a quencher; (ii) the probes comprise nucleic acid molecules; (iii) the substrate is substantially planar and comprises an array of discrete locations at different addresses on the substrate, wherein the locations have attached thereto different probes and a fluorescent label that produces the signal, wherein the fluorescent label is in sufficient proximity to the probe whereby hybridization between an analyte and probe at the location causes FRET and/or quenching of the signal. In some embodiments, the fluorescent label is attached to the surface through the probe. In some embodiments, the fluorescent label is non-covalently attached to the probe. In some embodiments, the fluorescent label is not attached to the surface through the probe. In some embodiments, the concentration of the analyte in the fluid based on the kinetics of change of the signal over time.

In some embodiments of the method of the invention, the fluid volume further comprises competitor molecules labeled with a quencher, wherein the competitor molecules compete with the analytes for binding with the probes.

One aspect of the invention is a method of detecting binding between analyte molecules and an array of probe molecules comprising: (a) incubating the analyte molecules with the array of probe molecules, wherein binding between a analyte molecule and a probe molecule results in a change in a signal from the array; and (b) measuring the signal from the array over time during incubation. In some embodiments, binding between a target molecule and a probe molecule results in a decrease in a signal from the array. In some embodiments, binding between a target molecule and a probe molecule results in an increase in a signal from the array.

One aspect of the invention is a method of detecting binding between an analyte molecule and a probe comprising: (a) incubating an analyte molecule comprising a quencher of a donor-quencher pair with a probe immobilized on a surface of a solid substrate under conditions whereby the analyte molecule can bind to the probe, wherein the donor of the donor-quencher pair is immobilized on the surface at a distance from the immobilized probe and whereby binding between the analyte molecule and the probe quenches a signal from the donor, and wherein the donor is not directly coupled to the immobilized probe; and (b) measuring the signal. In some embodiments, the method comprises incubating a plurality of different analyte molecules with a plurality of different probes immobilized to different addressable locations on the surface of the substrate.

One aspect of the invention is a system comprising: (a) a device with (i) a solid support having a surface and (ii) a plurality of different probes, wherein the different probes are immobilized to the surface; (b) a fluid volume comprising an analyte wherein the fluid volume is in contact with the solid support, and (c) a detector assembly comprising means to detect signals measured at multiple time points from each of a plurality of spots on the microarray while the fluid volume is in contact with the solid support. In some embodiments, the signals measured at multiple time points detected by the detectors can be correlated with the binding of analyte to the probes.

In some embodiments the system further comprises: (d) an assembly that controls temperature of the solid support and/or the fluid volume. In some embodiments, the different probes are immobilized at different addressable locations.

In some embodiments the system further comprises: (e) a data acquisition system for acquiring and storing the data and (f) a computing system for analyzing the signals. In some embodiments, the plurality of detectors comprises an array of transducers. In some embodiments, the array of transducers is capable of measuring an electrochemical, electrical, mechanical, magnetic, acoustic, or optical signal. In some embodiments, the solid substrate is in contact with the array of transducers. In some embodiments, the transducer array spaced away from the solid substrate. In some embodiments, one or more transducers correspond to an addressable location. In some embodiments, the transducer array is an optical transducer array which is optically coupled to the solid substrate. In some embodiments, the optical transducer array is optically coupled to the solid substrate via one or more lenses.

In some embodiments, the system is capable of measuring a plurality of binding rates simultaneously. In some embodiments, the plurality of binding rates is used to determine the concentration of a plurality of analytes.

In some embodiments, the signal detected by the detector comprises an electrochemical, electrical, mechanical, magnetic, acoustic, or optical signal. In some embodiments, the signal is generated from cyclic voltammetry, impedance spectroscopy, or surface plasmon resonance systems. In some embodiments, the signal is an optical signal. In some embodiments, the signal is from fluorescence, absorption, or luminescence. In some embodiments, the signals measured at multiple time points, correlating to the binding of analyte are due, at least in part, to fluorescent resonance energy transfer (FRET). In some embodiments, the signals measured at multiple time points, correlating to the binding of analyte are due, at least in part, to quenching of a fluorescent signal. In some embodiments, the signals measured at multiple time points are due, at least in part, to the interaction between an analyte comprising a quenching moiety, and probe comprising a fluorescent moiety. In some embodiments, the moiety comprising the optical signal is covalently bound to the probe molecule. In some embodiments, the moiety comprising the optical signal is non-covalently bound, to the probe molecule. In some embodiments, the moiety comprising the optical signal is bound to the probe molecule through another molecule. In some embodiments, the moiety comprising the optical signal is bound to the substrate.

One aspect of the invention is a system comprising: an assay assembly comprising means to engage a microarray and means to perform an assay on a surface of the microarray; and a detector assembly comprising means to detect signals measured at multiple time points from each of a plurality of spots on the microarray during the performance of the assay. In some embodiments, the means to perform the assay comprise means to provide a compartment wherein the surface of the microarray comprises a floor of the compartment and means to deliver reagents and analytes into the compartment.

One aspect of the invention is a device comprising: a solid substrate having a surface and a plurality of different probes, wherein the different probes are immobilized to the surface at different addressable locations, the addressable locations comprise optical signal moieties bound to the surface, the optical signal moieties are not bound directly to the probes, and the optical signal from the optical signal moieties is capable of changing upon binding of an analyte to the probes. In some embodiments, the optical signal moiety comprises a dye, a luminescent moiety, or a fluorescent moiety.

One aspect of the invention comprises software comprising: (a) a computer executable code that accesses information about signals measured at multiple time points at each of a plurality of known locations on a microarray, wherein the signal intensity is a function of the number of binding events between analyte molecules and probe molecules attached to the microarray at known locations. In some embodiments, the software further comprises: (b) code that executes an algorithm that uses the information to determine the expected number of binding events before binding has reached saturation, the existence and number of analyte molecules in the solution and the existence of cross-hybridization. The algorithm furthermore can suppress the effects of cross-hybridization on the acquired data.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 shows a few samples of the real-time measurements of the microarray experiment where control target analytes are added to the system FIGS. 12-15 each show data for 4 different spots with similar oligonucletide capturing probes. The target DNA analyte is introduced in the system at time zero and quenching (reduction of signal) occurs only when binding happens.

DETAILED DESCRIPTION OF THE INVENTION

Introduction

Figure 1:
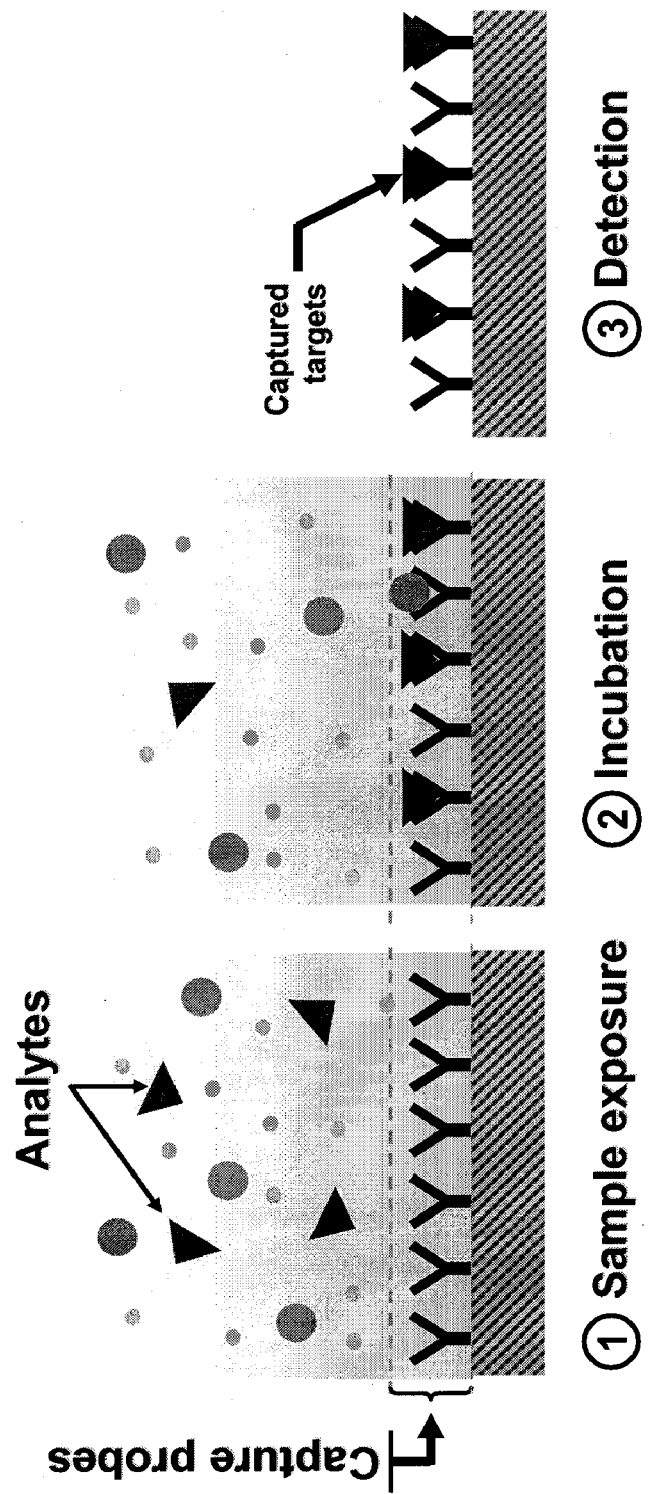
FIG. 1 shows conventional detection procedure in affinity-based biosensors where capturing probes are used to capture target analyte in the incubation phase, and detection is carried out in a dry-phase after completion of the incubation

The methods, devices, and systems disclosed herein concern the real-time measurements of target binding events in microarrays and parallel affinity-based biosensors. The methods and systems described herein can be referred to as real-time microarray (RT-µArray) systems. Real-time measurement of the kinetics of multiple binding events allows for an accurate and sensitive determination of binding characteristics or of analyte concentration for multiple species simultaneously. One aspect of present invention is the evaluation of the abundance of target analytes in a sample by the real-time detection of target-probe binding events. In certain embodiments, RT-µArray detection systems measure the concentration of the target analytes by analyzing the binding rates and/or the equilibrium concentration of the captured analytes in a single and/or plurality of spots. Some applications of RT-µArrays fall within the field of Genomics and Proteomics, in particular DNA and Protein microarrays. Some of the advantages of RT-µArray systems over conventional microarray platforms are in their higher detection dynamic range, lower minimum detection level (MDL), robustness, and lower sensitivity to array fabrication systematic errors, analyte binding fluctuation, and biochemical noise, as well as in the avoidance of the washing step required for conventional microarrays.

One aspect of the invention is a method of measuring binding of analytes to a plurality of probes on surface in "real time". As used herein in reference to monitoring, measurements, or observations of binding of probes and analytes of this invention, the term "real-time" refers to measuring the status of a binding reaction while that reaction is occurring, either in the transient phase or in biochemical equilibrium. Real time measurements are performed contemporaneously with the monitored, measured, or observed binding events, as opposed to measurements taken after a reaction is fixed. Thus, a "real time" assay or measurement contains not only the measured and quantitated result, such as fluorescence, but expresses this at various time points, that is, in hours, minutes, seconds, milliseconds, nanoseconds, etc. "Real time" includes detection of the kinetic production of signal, comprising taking a plurality of readings in order to characterize the signal over a period of time. For example, a real time measurement can comprise the determination of the rate of increase or decrease in the amount of analyte bound to probe.

The measurements are performed in real time with a plurality of probes and analytes. The invention is useful for measuring probes and analytes that bind specifically to one another. A probe and an analyte pair that specifically bind to one another can be a specific binding pair.

The methods and systems of the invention can be used for measuring the binding of multiple specific binding pairs in the same solution at the same time. In one embodiment of the invention a plurality of probes which are members of a specific binding pair are attached to a surface, and this surface is used to measure the binding kinetics of a plurality of analytes which comprise the other member of the specific binding pair.

One aspect of the invention is a method of measuring binding between analyte and probe which lowers, and in some cases eliminates the noise which is present in conventional microarrays and which decreases the quality of the analyte-probe binding information. In conventional microarrays and most of the affinity-based biosensors, the detection and incubation phases of the assay procedure are carried out at different times. As shown in FIG. 1, conventional detection is carried out in a dry-phase at the point where a scanning and/or imaging technique used to assess the captured targets.

Figure 2:
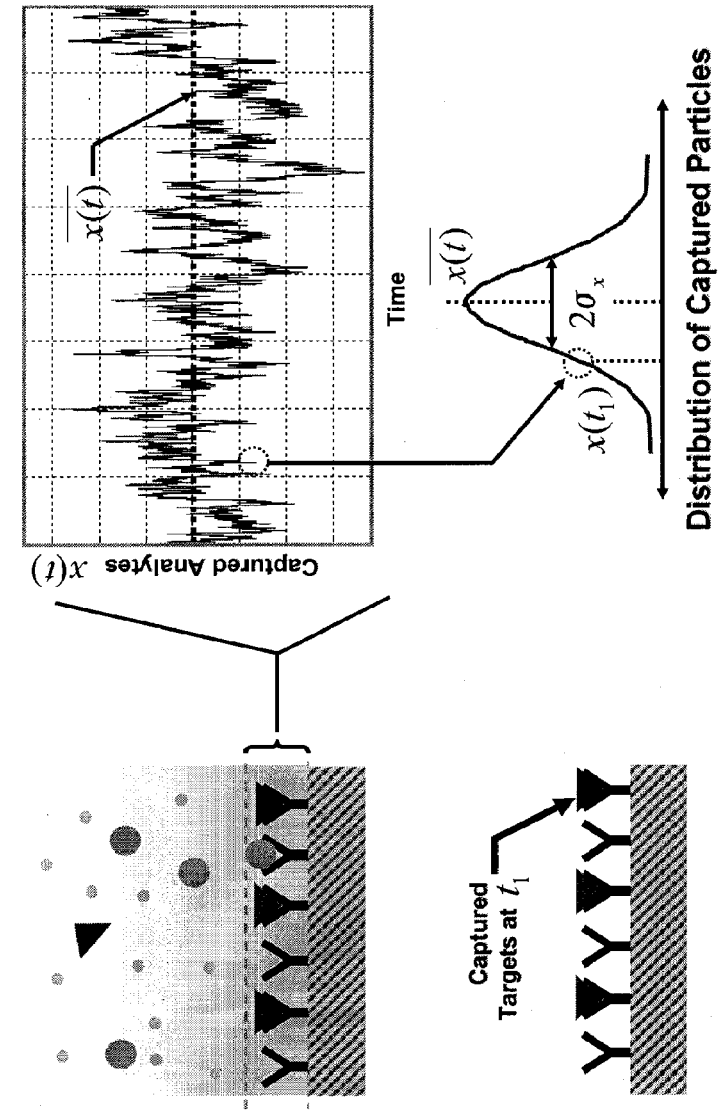
FIG. 2 shows conventional detection after completing incubation at time $t_1$ and the uncertainty associated with it.

The following analysis illustrates inherent problems with conventional microarray analysis techniques, and the advantages of the real time microarray systems of the present invention in improving the quality of the binding measurement. Let $x(t)$ denote the total number of captured analyte in a given spot of the microarray and/or affinity-based biosensor at a given time instant t. Furthermore, let $\overline{x(t)}$ denote the expected value of $x(t)$ when the incubation process has reached biochemical equilibrium. A typical microarray procedure is focused on estimating $\overline{x(t)}$, and using its value as an indication of the analyte concentration in the sample; in fact, most data analysis techniques deduce their results based on $\overline{x(t)}$. Nevertheless, if we measure the number of captured analytes at time $t_1$ in the equilibrium, for any given microarray spot it holds that $x(t_1) \neq \overline{x(t)}$. This is due to the inherent biochemical noise and other uncertainties of the system. This phenomenon is illustrated in FIG. 2, where the number of captured analytes in each spot of the microarray fluctuates in time, even in biochemical equilibrium. Accordingly, a single measurement taken at time $t_1$, which is what conventional microarray experiments provide, essentially samples a single point of the random process of analyte binding.

Figure 3:
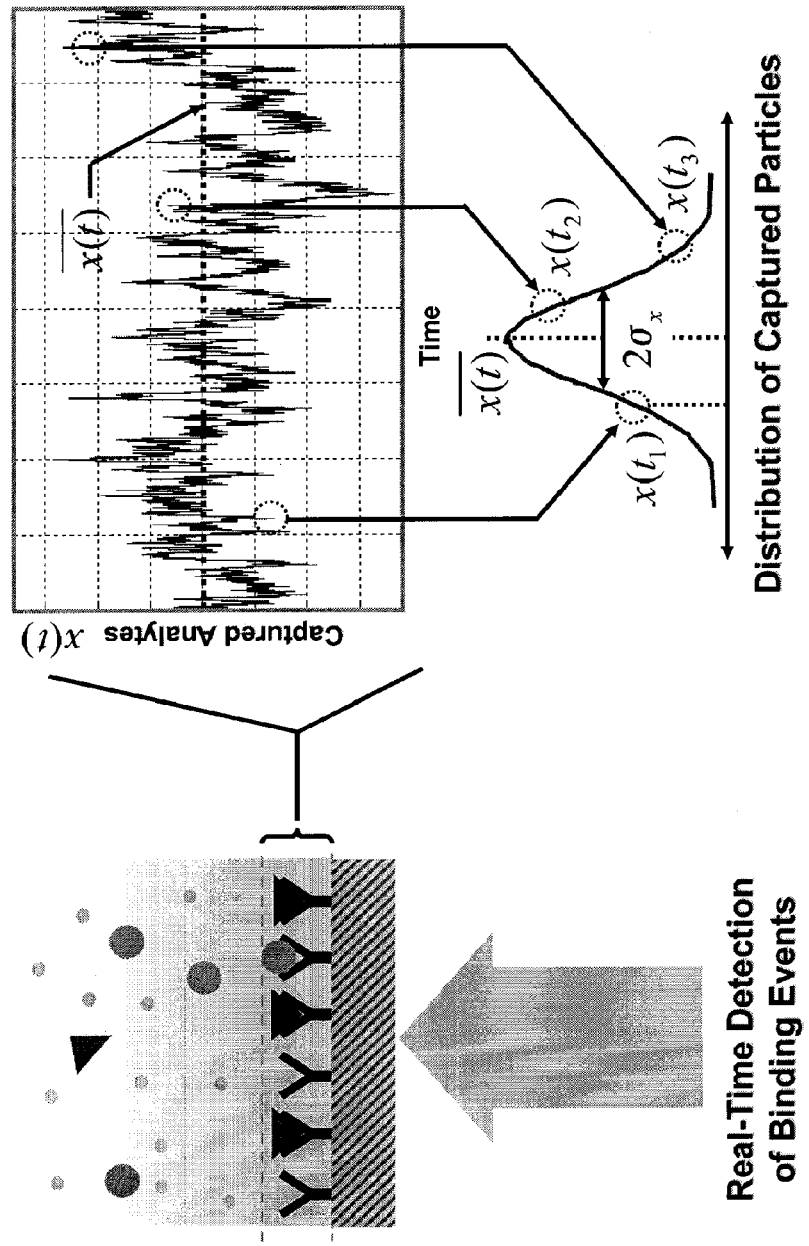
FIG. 3 shows that in real-time microarray systems of the present invention, multiple measurement of the number of captured analytes can be carried out, without the necessity of stopping the incubation step.

Now, consider the case where we are able measure $x(t)$ multiple times, in real-time without the necessity of stopping the incubation and analyte binding reaction. This platform, which we call the real-time microarrays (RT-µArrays), has many advantages over the conventional method. In some embodiments of RT-µArrays, the kinetic of the bindings can be observed. Therefore, one can test whether the system has reached biochemical equilibrium or not. In other embodiments, multiple samples of $x(t)$ are measured (see FIG. 3), and different averaging techniques and/or estimation algorithms can be used to estimate $\overline{x(t)}$ and other characteristics of process $x(t)$.

Figure 4:
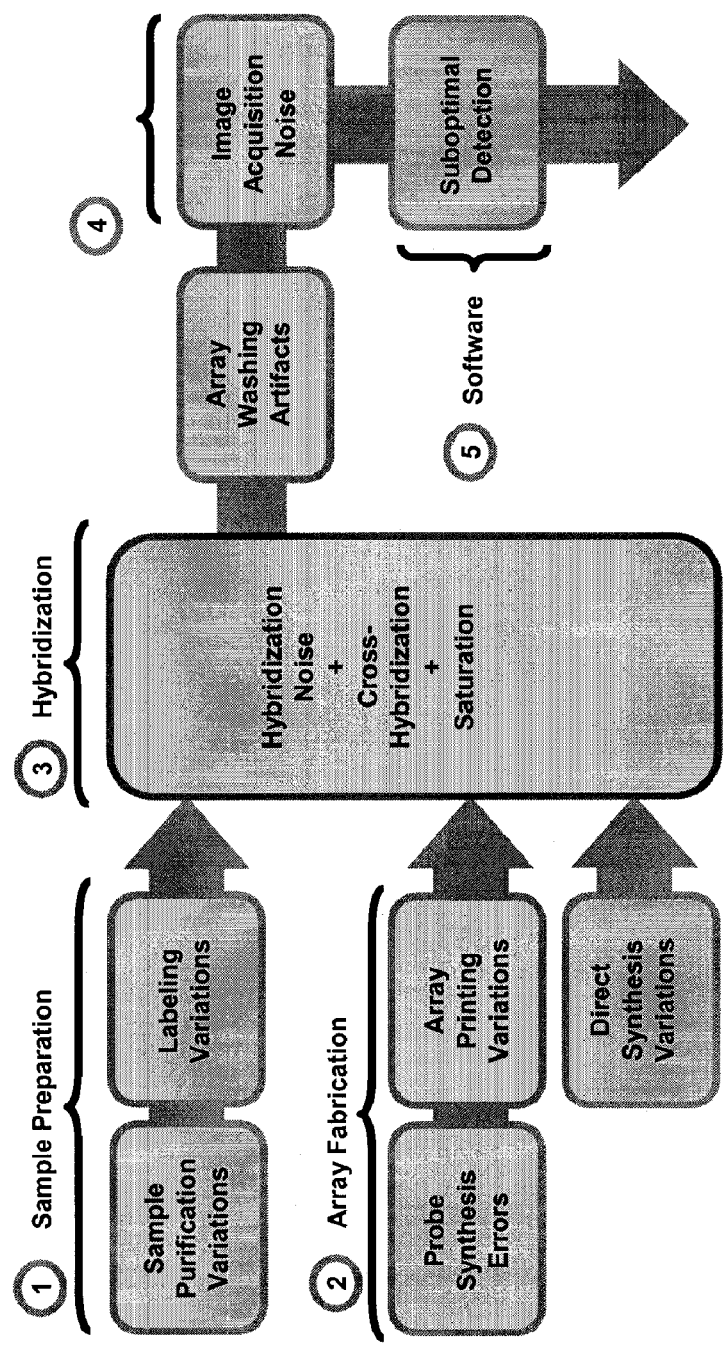
FIG. 4 shows a block diagram of the errors associated with conventional DNA microarrays.

FIG. 4 shows a block diagram of the errors associated with conventional DNA microarrays. These may be categorized into three stages: pre-hybridization (steps 1 and 2), hybridization (step 3), and post-hybridization (steps 4 and 5). The pre-hybridization errors arise from sample purification variations and the errors or variations in reverse transcribing mRNA to cDNA, in generating in vitro transcribed RNA complementary to the cDNA (cRNA, or IVT RNA), and or in labeling the analytes (step 1), and the errors arising from non-uniform probe spotting and or synthesis on the array (step 2). The hybridization errors arise from the inherent biochemical noise, cross-hybridization to similar targets, and the probe saturation (step 3). Post-hybridization errors include washing artifacts, image acquisition errors (step 4), and suboptimal detection (step 5). The most critical of these are probe density variations (step 2), probe saturation and cross-hybridization (step 3) and washing artifacts (step 4).

The methods and systems of the present invention can compensate for all the above errors except for those of sample preparation (step 1). Probe density variations can be measured prior to incubation and therefore accounted for in post-processing (step 5), incubation noise can be reduced by taking many samples (rather than a single one), as mentioned earlier, probe saturation can be avoided by estimating target concentrations from the reaction rates, and finally washing is avoided altogether.

One aspect of the invention is a method of measuring the binding of a plurality of analytes to a plurality of probes with a higher dynamic range than obtained with conventional microarrays. In some embodiments of the invention, the dynamic range is 3, 4, 5 or more orders of magnitude.

Methods

One aspect of the invention is a method comprising measuring binding of analytes to probes on a microarray in real-time. In one embodiment, the method comprises the steps of: contacting a fluid volume comprising a plurality of different analytes with a solid substrate comprising a plurality of different probes, wherein the probes are capable of specifically binding with the analytes; and measuring signals at multiple time points while the fluid volume is in contact with the substrate, wherein the signals measured at multiple time points can be correlated with the amount of binding of the analytes with the probes. One embodiment of the method further comprises using the signals measured at multiple time points to determine the concentration of an analyte in the fluid volume.

In one embodiment the method involves the use of probe arrays in which each addressable location emits a signal that is quenchable upon binding of an analyte. For example, the quenchable moiety (e.g., a fluorescent moiety) is attached to the probe on the array or in close physical proximity thereto. The surface of such array will emit signal from each addressable location which can be detected using, for example, a microscope and a light detector (e.g., a CCD camera or CMOS image sensor). The analytes in the sample are tagged with a quencher moiety that can quench the signal from the quenchable moiety. When the quencher does not, itself, emit a light signal, there is no signal from the fluid to interfere with the signal from the array. This diminishes the noise at the array surface. During the course of a binding reaction between analytes and substrate-bound probes, the signal at each addressable location is quenched. The signal at each addressable location is measured in real time, for example, by a CCD camera focused on the array surface. As the signal at any location changes as a result of binding and quenching, the change is measured. These measurements over time allow determination of the kinetics of the reaction which, in turn, allows determination of the concentration of analytes in the sample.

Alternatively if the analytes are labeled with a light-emitting reporter, such as a fluorescent label, signal at the surface of array resulting from binding of the labeled analyte molecules can be detected by properly focusing the detector at the array surface, thereby minimizing the noise from signal in solution.

In another embodiment, the probes are attached to the surface of an array comprising sensors, such as a CMOS sensor array, which produce electrical signals that change as a result of binding events on the probes. This also affords real time measurement of a plurality of signals on an array (Hassibi and Lee, IEEE Sensors journal, 6-6, pp. 1380-1388, 2006, and Hassibi, A. "Integrated Microarrays," Ph.D. Thesis Stanford University, 2005.

Accordingly, the methods of this invention allow real time measurements of a plurality of binding events on an array of probes on a solid support.

Analyte and Probe

The terms "probe" and "analyte" as used herein refer to molecular species that bind to one another in solution. A single probe or a single analyte is generally one chemical species. That is, a single analyte or probe may comprise many individual molecules. In some cases, a probe or analyte may be a set of molecules that are substantially identical. In some cases a probe or analyte can be a group of molecules all of which have a substantially identical binding region. A "probe" and/or "analyte" can be any pair of molecules that bind to one another, including for example a receptor/ligand pair, or a hybridizing pair of nucleic acids. In probes of the present invention are bound to a solid surface. The analyte is in solution, and can also be referred to as the target or the target analyte. Thus, while the probe and analyte can interchangeably be the different members of any binding pair, in some cases it is more advantageous for one or the other to be the probe or the analyte, for instance where the molecule is more easily coupled to the surface, it can be advantageous for that molecule to be the probe, or where a molecule is more soluble in the solution of interest, it can be advantageous for that molecule to be the analyte.

The probes or analytes can be any type of chemical species. The probes or analytes are generally biomolecules such as nucleic acids, proteins, carbohydrates, lipids, or small molecules. The probe and analyte which bind to one another can each be the same or different types of species. The analyte or probe may be bound to another type of molecule and may comprise different molecules. For example, an analyte could be a protein carbohydrate complex, or a nucleic acid connected to protein. A probe-analyte pair can also be a receptor-ligand pair. Where the chemical species is large or made of multiple molecular components, the probe or analyte may be the portion of the molecule that is capable of binding, or may be the molecule as a whole. Examples of analytes that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, antibodies, and hybridizing nucleic acids.

The term "probe" is used herein to refer to the member of the binding species that is attached to the substrate. For instance, the probe consists of biological materials deposited so as to create spotted arrays; and materials synthesized, deposited, or positioned to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media. The construction of various probe arrays of the invention are described in more detail below.

In some embodiments, the probe and/or the analyte comprises a polynucleotide. The terms "polynucleotide," "oligonucleotide," "nucleic acid" and "nucleic acid molecule" as used herein include a polymeric form of nucleotides of any length, either ribonucleotides (RNA) or deoxyribonucleotides (DNA). This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and U.S. Pat. No. 5,644, 048), phosphorodithioate (Briu et al., J. Am. Chem. Soc. 11 1:2321 (1989), O-methylphosphoroamidite linkages (see Eckstein, Oligonucleotides and Analogues: A Practical Approach, Oxford University Press), and peptide nucleic acid backbones and linkages (see Carlsson et al., Nature 380:207 (1996)). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). These modifications of the ribose-phosphate backbone may be done to facilitate the addition of labels, or to increase the stability and half-life of such molecules in physiological environments.

In some embodiments of the invention, oligonucleotides are used. An "oligonucleotide" as used herein is a single-stranded nucleic acid ranging in length from 2 to about 1000 nucleotides, more typically from 2 to about 500 nucleotides in length. In some embodiments, it is about 10 to about 100 nucleotides, and in some embodiments, about 20 to about 50 nucleotides.

In some embodiments of the invention, for example, expression analysis, the invention is directed toward measuring the nucleic acid concentration in a sample. In some cases the nucleic acid concentration, or differences in nucleic acid concentration between different samples, reflects transcription levels or differences in transcription levels of a gene or genes. In these cases it can be desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In some embodiments, where it is desired to quantify the transcription level (and thereby expression) of one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript or large differences of changes in nucleic acid concentration are desired, no elaborate control or calibration is required.

In the simplest embodiment, such a nucleic acid sample is the total mRNA or a total cDNA isolated and/or otherwise derived from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of Laboratory Techniques in Biochemistry and Molecular Biology Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

In some embodiments, the probe and or the analyte may comprise a polypeptide. As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. The "peptide" refers to polypeptides of no more than about 50 amino acids, while term "protein" refers to longer polypeptides, typically with three-dimensional structures. Non-natural polypeptides containing one or more analogs of an amino acid (including, for example, unnatural amino acids, etc.), can also be useful in the invention, as can polypeptides with substituted linkages, as well as other modifications known in the art, both naturally occurring and non-naturally occurring. Polypeptides and proteins can have specific binding properties. For instance, an enzyme can have a region that binds specifically with a substrate, and/or has regions that bind to other proteins, such as the binding of enzyme subunits. Antibodies, which can have very specific binding properties are also polypeptides.

In some embodiments the probe and/or analyte can comprise a carbohydrate such as a polysaccharide. The term polysaccharide, as used herein, refers to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Monosaccharides include, but are not limited to, ribose, 2-deoxy-ribose, glucose, mannose, xylose, galactose, fucose, fructose, etc. Disaccharides contain two monosaccharide units joined by a glycosidic linkage. Disaccharides include, for example, sucrose, lactose, maltose, cellobiose, and the like. oligosaccharides typically contain from 2 to 10 monosaccharide units joined in glycosidic linkage. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc. A saccharide may also reside as a component part of a larger molecule, for example, as the saccharide moiety of a nucleoside, a nucleotide, a polynucleotide, a DNA, an RNA, etc.

In some embodiments, the analyte and/or probe is a small molecule. Generally the small molecule will be an organic molecule, for example, biotin or digoxigenin, but in some cases, the analyte can be inorganic, for example an inorganic ion such as lithium, sodium, ferric, ferrous, etc. The small molecule can also be an organometallic compound, having both inorganic and organic components.

Probes on a Solid Substrate

For the methods of the present invention, the probes are attached to a solid substrate. The solid substrate may be biological, nonbiological, organic, inorganic, or a combination of any of these, existing as particles, strands, precipitates, gels, sheets, tubing, spheres, containers, capillaries, pads, slices, films, plates, slides, semiconductor integrated chips etc. The solid substrate is preferably flat but may take on alternative surface configurations. For example, the solid substrate may contain raised or depressed regions on which synthesis or deposition takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$ $SiN_4$, modified silicon, or any one of a variety of gels or polymers such as (poly)tetrafluoroethylene, (poly)vinylidendifluoride, polystyrene, polycarbonate, or combinations thereof. The solid support and the chemistry used to attach the solid support are described in detail below.

The substrate can be a homogeneous solid and/or unmoving mass much larger than the capturing probe where the capturing probes are confined and/or immobilized within a certain distance of it. The mass of the substrate is generally at least 100 times larger than capturing probes mass. In certain embodiments, the surface of the substrate is planar with roughness of 0.1 nm to 100 nm, but typically between 1 nm to 10 nm. In other embodiments the substrate can be a porous surface with roughness of larger than 100 nm. In other embodiments, the surface of the substrate can be non-planar. Examples of non-planar substrates are spherical magnetic beads, spherical glass beads, and solid metal and/or semiconductor and/or dielectric particles.

For the methods of the present invention, the plurality of probes may be located in one addressable region and/or in multiple addressable regions on the solid substrate. In some embodiments the solid substrate has about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 addressable regions with probes.

In some embodiments it is also useful to have addressable regions which do not contain probe, for example, to act as control spots in order to increase the quality of the measurement, for example, by using binding to the spot to estimate and correct for non-specific binding.

Analyte/Probe Binding

The methods of the present invention are directed toward measuring the binding characteristics of multiple probes and analytes in real time. The method is particularly useful for characterizing the binding of probes and analytes which specifically bind to one another. As used herein, a probe "specifically binds" to a specific analyte if it binds to that analyte with greater affinity than it binds to other substances in the sample.

The binding between the probe and the analyte in the present invention occurs in solution. Usually the probe and analyte are biomolecules and the solution is an aqueous solution. An aqueous solution is a solution comprising solvent and solute where the solvent is comprised mostly of water. The methods of the invention, however, can be used in any type of solution where the binding between a probe and an analyte can occur and be observed.

Molecular recognition assays generally involve detecting binding events between two types of molecules. The strength of binding can be referred to as "affinity". Affinities between biological molecules are influenced by non-covalent intermolecular interactions including, for example, hydrogen bonding, hydrophobic interactions, electrostatic interactions and Van der Waals forces. In multiplexed binding experiments, such as those contemplated here, a plurality of analytes and probes are involved. For example, the experiment may involve testing the binding between a plurality of different nucleic acid molecules or between different proteins. In such experiments analytes preferentially will bind to probes for which they have the greater affinity. Thus, determining that a particular probe is involved in a binding event indicates the presence of an analyte in the sample that has sufficient affinity for the probe to meet the threshold level of detection of the detection system being used. One may be able to determine the identity of the binding partner based on the specificity and strength of binding between the probe and analyte.

The binding may be a receptor-ligand, enzyme-substrate, antibody-antigen, or a hybridization interaction. The probe/analyte binding pair or analyte/probe binding pair can be nucleic acid to nucleic acid, e.g. DNA/DNA, DNA/RNA, RNA/DNA, RNA/RNA, RNA. The probe/analyte binding pair or analyte/probe binding pair can be a nucleic acid and a polypeptide, e.g. DNA/polypeptide and RNA/polypeptide, such as a sequence specific DNA binding protein. The probe/analyte binding pair or analyte/probe binding pair can be any nucleic acid and a small molecule, e.g. RNA/small molecule, DNA/small molecule. The probe/analyte binding pair or analyte/probe binding pair can be any nucleic acid and synthetic DNA/RNA binding ligands (such as polyamides) capable of sequence-specific DNA or RNA recognition. The probe/analyte binding pair or analyte/probe binding pair can be a protein and a small molecule or a small molecule and a protein, e.g. an enzyme or an antibody and a small molecule.

The probe/analyte binding pair or analyte/probe binding pair can be a carbohydrate and protein or a protein and a carbohydrate, a carbohydrate and a carbohydrate, a carbohydrate and a lipid, or lipid and a carbohydrate, a lipid and a protein, or a protein and a lipid, a lipid and a lipid.

The analyte/probe binding pair can comprise natural binding compounds such as natural enzymes and antibodies, and synthetic binding compounds. The probe/analyte binding pair or analyte/probe binding pair can be synthetic protein binding ligands and proteins or proteins and synthetic binding ligands, synthetic carbohydrate binding ligands and carbohydrates or carbohydrates and synthetic carbohydrate binding ligands, synthetic lipid binding ligands or lipids and lipids and synthetic lipid binding ligands.

Nucleic Acid Systems

One particularly useful aspect of the present invention involves specific hybridization between an analyte and a probe, where both comprise nucleic acids.

As used herein an "oligonucleotide probe" is an oligonucleotide capable of binding to a target nucleic acid of complementary sequence through one or more types of chemical bonds, usually through complementary base pairing, usually through hydrogen bond formation. The oligonucleotide probe may include natural (i.e. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages. The oligonucleotide probes can also comprise locked nucleic acids (LNA), LNA, often referred to as inaccessible RNA, is a modified RNA nucleotide. The ribose moiety of the LNA nucleotide is modified with an extra bridge connecting 2' and 4' carbons. The bridge "locks" the ribose in 3'-endo structural conformation, which is often found in A-form of DNA or RNA. LNA nucleotides can be mixed with DNA or RNA bases in the oligonucleotide. Such oligomers are commercially available. The locked ribose conformation can enhance base stacking and backbone pre-organization, and can increase the thermal stability (melting temperature) of oligonucleotides.

The term "nucleic acid analyte" or "target nucleic acid" or "target" refers to a nucleic acid (often derived from a biological sample and hence referred to also as a sample nucleic acid), to which the oligonucleotide probe specifically hybridizes. It is recognized that the target nucleic acids can be derived from essentially any source of nucleic acids (e.g., including, but not limited to chemical syntheses, amplification reactions, forensic samples, etc.). It is either the presence or absence of one or more target nucleic acids that is to be detected, or the amount of one or more target nucleic acids that is to be quantified. The target nucleic acid(s) that are detected preferentially have nucleotide sequences that are complementary to the nucleic acid sequences of the corresponding probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. The difference in usage will be apparent from context.

In the present invention, the specific hybridization of an oligonucleotide probe to the target nucleic acid can be measured in real-time. An oligonucleotide probe will generally hybridize, bind, or duplex, with a particular nucleotide sequence under stringent conditions even when that sequence is present in a complex mixture. The term "stringent conditions" refers to conditions under which a probe will hybridize preferentially to its target subsequence, and to a lesser extent to, or not at all to, other sequences.

For nucleic acid systems, the oligonucleotide probes of the present invention are designed to be complementary to a nucleic acid target sequence, such that hybridization of the target sequence and the probes of the present invention occurs. This complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, an oligonucleotide probe that is not substantially complementary to a nucleic acid analyte will not hybridize to it under normal reaction conditions.

The methods of the present invention thus can be used, for example, to determine the sequence identity of a nucleic acid analyte in solution by measuring the binding of the analyte with known probes. The sequence identity can be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity.

The methods of the current invention when applied to nucleic acids, can be used for a variety of applications including, but not limited to, (1) mRNA or gene expression profiling, involving the monitoring of expression levels for example, for thousands of genes simultaneously. These results are relevant to many areas of biology and medicine, such as studying treatments, diseases, and developmental stages. For example, microarrays can be used to identify disease genes by comparing gene expression in diseased and normal cells; (2) comparative genomic hybridization (Array CGH), involving the assessment of large genomic rearrangements; (3) SNP detection arrays for identifying for Single Nucleotide Polymorphisms (SNP's) in the genome of populations; and chromatin immunoprecipitation (chIP) studies, which involve determining protein binding site occupancy throughout the genome, employing ChIP-on-chip technology.

The present invention can be very sensitive to differences in binding between nucleic acid species, in some cases, allowing for the discrimination down to a single base pair mismatch. And because the present invention allows the simultaneous measurement of multiple binding events, it is possible to analyze several species simultaneously, where each is intentionally mismatched to different degrees. In order to do this, a "mismatch control" or "mismatch probe" which are probes whose sequence is deliberately selected not to be perfectly complementary to a particular target sequence can be used, for example in expression arrays. For each mismatch (MM) control in an array there, for example, exists a corresponding perfect match (PM) probe that is perfectly complementary to the same particular target sequence. In "generic" (e.g., random, arbitrary, haphazard, etc.) arrays, since the target nucleic acid(s) are unknown, perfect match and mismatch probes cannot be a priori determined, designed, or selected. In this instance, the probes can be provided as pairs where each pair of probes differs in one or more pre-selected nucleotides. Thus, while it is not known a priori which of the probes in the pair is the perfect match, it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3, 4, 5, or more) of probes that differ from each other in particular preselected nucleotides. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

It will be understood by one of skill in the art that control of the characteristics of the solution such as the stringency are important in using the present invention to measure the binding characteristics of a analyte-probe pair, or the concentration of a nucleic acid analyte (target nucleic acid). A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). In some embodiments, highly stringent conditions are used. In other embodiments, less stringent hybridization condition; for example, moderate or low stringency conditions may be used, as known in the art; see Maniatis and Ausubel, supra, and Tijssen, supra. The hybridization conditions may also vary when a non-ionic backbone, i.e. PNA is used, as is known in the art.

Stringent conditions are sequence-dependent and will be different in different circumstances. Longer sequences tend to hybridize specifically at higher temperatures. Generally, stringent conditions can be selected to be about 5.degree. C. lower than the thermal melting point ($T_m$) for the specific sequence at a defined ionic strength and pH. The $T_m$, is the temperature (under defined ionic strength, pH, and nucleic acid concentration) at which 50% of the probes complementary to the target sequence hybridize to the target sequence at equilibrium. (As the target analyte sequences are generally present in excess, at $T_m$, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

In some embodiments, the probe and or the analyte may comprise an antibody. As used herein, the term "antibody" refers to an immunoglobulin molecule or a fragment of an immunoglobulin molecule having the ability to specifically bind to a particular molecule, referred to as an antigen. The antibody may be an anti-receptor antibody specific for the receptor used in the assay. Thus, the antibody may be capable of specifically binding the receptor as the antigen. Antibodies and methods for their manufacture are well known in the art of immunology. The antibody may be produced, for example, by hybridoma cell lines, by immunization to elicit a polyclonal antibody response, or by recombinant host cells that have been transformed with a recombinant DNA expression vector that encodes the antibody. Antibodies include but are not limited to immunoglobulin molecules of any isotype (IgA, IgG, IgE, IgD, IgM), and active fragments including Fab, Fab', F(ab')$_2$, Facb, Fv, ScFv, Fd, $V_H$ and $V_L$. Antibodies include but are not limited to single chain antibodies, chimeric antibodies, mutants, fusion proteins, humanized antibodies and any other modified configuration of an immunoglobulin molecule that comprises an antigen recognition site of the required specificity.

The preparation of antibodies including antibody fragments and other modified forms is described, for example, in "Immunochemistry in Practice," Johnstone and Thorpe, Eds., Blackwell Science, Cambridge, Mass., 1996; "Antibody Engineering," 2.sup.nd edition, C. Borrebaeck, Ed., Oxford University Press, New York, 1995; "Immunoassay", E. P. Diamandis and T. K. Christopoulos, Eds., Academic Press, Inc., San Diego, 1996; "Handbook of Experimental Immunology," Herzenberg et al., Eds, Blackwell Science, Cambridge, Mass., 1996; and "Current Protocols in Molecular Biology" F. M. Ausubel et al., Eds., Greene Pub. Associates and Wiley Interscience, 1987, the disclosures of which are incorporated herein. A wide variety of antibodies also are available commercially.

In some embodiments, the probe and or the analyte may comprise two proteins. Protein-protein interactions can enable two or more proteins to associate. A large number of non-covalent bonds can form between the proteins when two protein surfaces are precisely matched, and these bonds account for the specificity of recognition. Protein-protein interactions are involved, for example, in the assembly of enzyme subunits; of multiprotein enzymatic complexes, or of molecular machines; in enzyme-substrate reactions; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions. For example, some oncogenes encode protein kinases whose enzymatic activity on cellular target proteins leads to the cancerous state. Another example of a protein-protein interaction occurs when a virus infects a cell by recognizing a polypeptide receptor on the surface, and this interaction has been used to design antiviral agents. In some cases, protein-protein interactions can be dependent on protein modifications. For example, histone proteins can be modified at different positions with different chemical tags (e.g. phosphorylation, or methylation), and the modifications themselves be required or involved in the recognition by other proteins (e.g chromatin remodeling and associated proteins).

Binding Kinetics

One aspect of the current invention is the use of the measurement of the binding kinetics to characterize binding of multiple probes and analytes in solution. The term "binding kinetics" as used herein refers to the rate at which the binding of the analyte to the probe occurs in a binding reaction. The term "binding reaction" as used herein describes the reaction between probes and analytes. In some cases, binding reaction refers to the concurrent binding reactions of multiple analytes and probes, and in other cases, the term binding reaction refers to the reaction between a single probe with a single analyte. The meaning will be clear from the context of use. The kinetic measurements can be expressed as the amount of analyte bound to the probe as a function of time. The binding kinetics can provide information about the characteristics of the probe-analyte binding such as the strength of binding, the concentration of analyte, the competitive binding of an analyte, the density of the probes, or the existence and amount of cross-hybridization.

In order to determine binding kinetics, the signal at multiple time points must be determined. The signal at least two time points is required. In most cases, more than two time points will be desired in order to improve the quality of the kinetic information. In some embodiments the signal at, 2-10, 10-50, 50-100, 100-200, 200-400, 400-800, 800-1600, 1600-3200, 3200-6400, 6400-13000, or higher than 13,000 time points will be measured. One of ordinary skill in the art can determine the effective number of points for a given embodiment. For example, where few points are obtained, the quality of information about the binding event can be low, but where the number of data points is very high, the data quality may be high, but the handling, storage, and manipulation of the data can be cumbersome.

The frequency at which the signal is measured will depend on the kinetics of the binding reaction or reactions that are being monitored. As the frequency of measurements gets lower, the time between measurements gets longer. One way to characterize a binding reaction is to refer to the time at which half of the analyte will be bound ($t_{1/2}$). The binding reactions of the invention can have a ($t_{1/2}$) from on the order of milliseconds to on the order of hours, thus the frequency of measurements can vary by a wide range. The time between measurements will generally not be even over the time of the binding reaction. In some embodiments, a short time between of measurements will be made at the onset of the reaction, and the time between measurements will be longer toward the end of the reaction. One advantage of the present invention is the ability to measure a wide range of binding rates. A high initial frequency of measurements allows the characterization of fast binding reactions which may have higher binding, and lower frequency of measurements allows the characterization of slower binding reactions. For example, points can initially be measured at a time between points on the order of a microsecond, then after about a millisecond, points can be measured at a time between points on the order of a millisecond, then after about a second, time points can be measured at a time between points on the order of a second. Any function can be used to ramp the change in measurement frequency with time. In some cases, as described below, changes in the reaction conditions, such as stringency or temperature changes will be made during a reaction, after which it may be desirable to change the frequency of measurements to measure the rates of reaction which will be changed by the change in reaction condition.

In some embodiments, a probe will have substantially no analyte bound to it at the beginning of the binding reaction, then the probe will be exposed to a solution containing the analyte, and the analyte will begin to bind, with more analyte bound to the probe with time. In some cases, the reaction will reach saturation, the point at which all of the analyte that is going to bind has bound. Generally, saturation will occur when a reaction has reached steady state. At steady state, in a given time period, just as many analytes are released as new analytes are bound (the on rate and off rate are equal). In some cases, with very strong binding, where the off-rate for the analyte is essentially zero, saturation will occur when substantially all of the analyte that can bind to the probe will have bound, has bound. Thus, while it is advantageous to measure a change in signal with time that can be correlated with binding kinetics, the measurement of a signal that does not change with time also provides information in the context of a real-time experiment, and can also be useful in the present invention. For example, in some cases the absence of a change in the signal will indicate the level of saturation. In other cases the absence of a change in signal can indicate that the rate of the reaction is very slow with respect to the change in time measured. It is thus a beneficial aspect of this invention to measure binding event in real time both where signals change with time and where the signals do not change with time.

One aspect of the methods of the present invention is the measurement of concentration of an analyte from the measurement of binding kinetics. Since analyte binding rate can be concentration-dependant, we can estimate the analyte abundance in the sample solution using binding rates.

In some embodiments, the concentration of analyte can be determined by equations relating to the kinetics of the hybridization process. For example, suppose that the number of probes at a particular spot on the array prior to any hybridization is given by $P_0$. The probability of a specific target binding to the probe site is given by $$\text{Prob(binding)} = k \cdot \text{Prob(target and probe in close proximity)} \cdot \text{Prob(probe is free)}, \quad (1)$$

where $k \leq 1$ depends of the bonds between the probe and the target and essentially a function of temperature, incubation conditions, and probe density. Here, the first probability is proportional to the number of target molecules available whereas the second probability is $$\text{Prob (probe is free)} = P(t)/P_0, \quad (2)$$

where $P(t)$ is the number of available probes at time t, i.e., those are not yet bound to any target. If we thus denote the forward and backwards target/probe binding reaction rates by $K_+$ and $K_-$, respectively, we may write the following differential equation for the available probe concentration $P(t)$:

$$dP(t)/dt = -K_+/P_0 P(t)(C-P_0-P(t)) + K_-(P_0-P(t)) \quad (3)$$

where C is the original target quantity in the solution so that $C-(P_0-P(t))$ represents the available target density at time t. The above is a Riccati differential equation that can be solved in closed form. However, instead of doing so, we can note that for small values of t we have $P(t) \approx P_0$, so that the differential equation becomes $$dP(t)/dt = -K_+/P_0(P(t)C). \qquad (4)$$

This a first-order linear differential equation with time constant $t = P_0/K_+C$. Accordingly, the target density can be determined from the reaction rate (or time constant) of P(t). In other words, using many sample measurements of P(t) at different times and fitting them to the curve $$P(t) = P_0 \exp(-K_+C/P_0)t \qquad (5)$$

allows us to estimate the target quantity C. In this case, the reaction rate (or inverse of the time constant) is proportional to the target concentration and inversely proportional to the probe density, something that has been observed in experiments.

One can also attempt to estimate C from the steady-state value of P(t), i.e., $P_\infty$. This can be found by setting $dP(t)/dt=0$ in the original Riccati equation which leads to a quadratic equation for $P_\infty$. In some simple cases, the solution to this quadratic equation can be considerably simplified.

When the target concentration is low: In this case, we can assume $P_0 \gg C$, so that we obtain $$P_\infty = P_0 - C, \qquad (6)$$

i.e., the reduction in available probes is equal to the target concentration.

When the target concentration is high: In this case, we can assume that $P_0 \ll C$, so that we obtain $$P_\infty = \frac{K_-}{K_+} \cdot \frac{P_0^2}{C}. \qquad (6)$$

In this case, the number of remaining probes is inversely proportional o the target concentration. This corresponds to probe saturation, which generally is not as good a method of determining C as determining C based on the reaction rate near the beginning of the reaction.

One aspect of the present invention is the determination of the binding of analyte to probe by measuring the rate near the beginning of the reaction. In addition to providing a more reliable estimate of C, measurement near the beginning of the reaction can shorten the time that is required to measure analyte binding over the time required for measuring binding from saturation. In some embodiments of the invention, the binding is measured during the time for less than about the first 0.1, 0.5, 1, 2, 3, 4, 5, 6, 8, 10, 12, 14, 18, 20, 25, 30, 40, 50, 60, 70, 80, or 90 percent of the analyte to bind as compared to the amount of analyte bound at saturation. In some embodiments, the binding kinetics are determined in a time for less than about the first 20% of the analyte to bind. In some embodiments, the binding kinetics are determined in a time for less than about the first 1-2% of the analyte to bind.

Changing Conditions During the Binding Experiment

One aspect of the methods of the present invention is a step of changing the conditions during the binding experiment. In conventional microarrays where only the end-point is determined, only a single set of binding conditions can be tested. In the methods of the present invention, the binding conditions can be changed in order to explore multiple sets of binding conditions during the same binding experiment. The condition which is changed can be, for example, any condition that affects the rate of binding of analyte to probe. The condition which is changed can be, for example, temperature, pH, stringency, analyte concentration, ionic strength, an electric field, or the addition of a competitive binding compound.

In some embodiments, the condition that is changed changes the rate of binding or hybridization. When measuring the binding of multiple analytes to probes in the same binding medium, as in the present invention, the kinetics of binding can vary widely for different analyte-probe combinations. The binding rate conditions can be varied, for example, by changing the temperature, concentration, ionic strength, pH, or by applying an electric potential. The binding rates for the different analytes can in some cases vary by many orders of magnitude, making it difficult and time consuming to measure the binding of all the analytes in one binding experiment. This ability to change the rate conditions can be used to improve the measurement of binding for multiple analytes that bind at different rates, for example by performing the initial part of the experiment under slower rate conditions, such that rapidly binding analytes can be readily measured, then raising the rate conditions such that more slowly binding analytes can be readily measured. This method of changing the binding rate during the binding experiment can also be used for better characterization of a single analyte or single set of analytes in solution, for instance, using binding rate conditions to measure the initial portion of the binding kinetics, then increasing the binding rate conditions to measure the later portion of the binding kinetics for a single analyte, for example, to establish the level of saturation. It will be understood by those of skill in the art that this method of changing the rate conditions can result in both improved quality of measurements, such as the measurement of analyte concentration, and/or in a savings of time. With the present method, for example by measuring the kinetics of binding, then changing the conditions to increase the rate of binding of weaker binding species, the time of the binding experiment can be reduced by greater than about 10%, 20%, 50%, 75%, or by a factor of 2, 4, 8, 10, 50, 100, 1000 or greater than 1000 over the times needed to obtain the same quality information using end-point binding methods.

In some embodiments, the condition that is changed is the stringency. As described above, the stringency can be changed by many factors including temperature, ionic strength, and the addition of compounds such as formamide. In some embodiments of the present invention, the medium is at one stringency at the beginning of the binding reaction, and at a later point the stringency of the medium is changed. This method can be used where different analytes or sets of analytes have different hybridization characteristics, for example, allowing the measurement of the binding of one set of analytes with a high stringency, then allowing the measurement of another set of analytes at a lower stringency in the same medium as part of the same binding experiment. This method can also be used for the characterization of binding for a single analyte by, for instance, measuring binding at high stringency at an initial portion of the binding reaction, then lowering the stringency and measuring a later portion of the binding reaction. The ability to change stringency can also be used to create conditions where a bound analyte becomes unbound, allowing, for instance, the measurement of the kinetics of binding at one stringency, followed by the measurement of release of the analyte into solution upon raising the stringency. This method also allows the binding of an analyte to a probe to be measured multiple times, for example, by measuring the kinetics of binding of the analyte under one set of stringency conditions, changing the stringency to release the analyte, for instance, by raising the stringency, then measuring the kinetics of binding of the analyte a subsequent time by changing the stringency conditions again, for example by lowering the stringency. Thus the ability to change the stringency during the binding reaction allows for the measurement of any number of binding and unbinding reactions with the same set of probes and analytes.

In some embodiments of the method of the present invention, an electric potential is applied during the binding reaction to the fluid volume to electrically change the stringency of the medium. In some embodiments, the system will provide an electrical stimulus to the capturing region using an electrode structure which is placed in proximity of the capturing region. If the analyte is an electro-active species and/or ion, the electrical stimulus can apply an electrostatic force of the analyte. In some embodiments the electrical potential is direct current (DC). In some embodiments, the electric potential is time-varying. In some embodiments the electric potential has both DC and time varying aspects. Their amplitude of the applied potential can be between 1 mV to 10V, but typically between 10 mV to 100 mV. The frequency of time-varying signal is between 1 Hz to 1000 MHz, but typically between 100 Hz to 100 kHz.

In some embodiments, the change in conditions is the addition of a competitive binding agent. For example, initially, a sample can be introduced which contains analyte that binds to a particular probe. The binding of that analyte can be monitored as described herein. Then, at any point during the binding of that analyte, an analyte that competes for the binding of that analyte to the probe can be added. The rate of displacement of the analyte by the competitive binding agent can then be measured, providing more information to characterize the binding of analyte to probe.

Detection of Signals

For the methods of the present invention, a signal is detected that can be correlated with the binding of analytes to the plurality of probes. The type of signals appropriate for the invention is any signal that can be amount of analyte bound to the plurality of probes. Appropriate signals include, for example, electrical, electrochemical, magnetic, mechanical, acoustic, or electromagnetic (light) signals. Examples of electrical signals useful in the present invention that can be correlated with analyte binding are capacitance and/or impedance. For example, analytes labeled with metals or metal clusters can change the capacitance and/or the impedance of a surface in contact with a fluid, allowing the amount of analyte bound to the probe on the surface to be determined. The electrical measurement can be made at any frequency including DC, 0-10 Hz, 10-100 Hz, 100-1000 Hz, 1 KHz-10 KHz, 10 KHz-100 KHz, 100 KHz-1 MHz, 1 MHz-10 MHZ, 10 MHz-100 MHz, 100 MHz-1 GHz, or above 1 GHz. In some embodiments, impedance spectroscopy can be used which obtains impedance versus frequency for any range of frequencies within the range of frequencies described above. Examples of electrochemical signals useful in the present invention that can be correlated with analyte binding include amperometric and voltammetric measurements, and/or measurements that involve the oxidation or reduction of redox species. For example, the analyte can be labeled with a compound which undergoes an oxidation or reduction reaction at a known redox potential, and the oxidative or reductive current can be correlated with the amount of analyte bound to surface probes. Examples of mechanical signals include the use of microelectomechanical (MEMS) devices. For example, the binding of analyte to probe on the surface of a small surface feature, such as a cantilever, can change the mass of the surface feature, the vibration frequency of which can then be correlated with the amount of analyte bound to the probe. Generally, the higher the mass, the lower the vibration frequency. Examples of acoustic signals include surface acoustic wave (SAW), and surface plasmon resonance signals. A surface acoustic wave (SAW) is an acoustic wave traveling along the surface of a material having some elasticity, with amplitude that typically decays exponentially with the depth of the substrate. The binding of labeled or unlabeled analyte to probe on a surface can change the SAW characteristics, e.g. amplitude, frequency in a manner that can be correlated with the amount of analyte bound to a probe. Surface plasmon resonance relies on surface plasmons, also known as surface plasmon polaritons, which are surface electromagnetic waves that propagate parallel, usually along a metal/dielectric interface. Since the wave is on the boundary of the metal and the external medium (water for example), these oscillations are very sensitive to any change of this boundary, such as the adsorption of molecules to the metal surface. The binding of labeled or unlabeled analyte to a probe attached to the surface can change the frequency of the resonant surface plasmon in a manner that can be correlated with the amount of analyte bound to the probes.

Particularly useful signals for the methods of the present invention are electromagnetic (light) signals. Examples of optical signals useful in the present invention are signals from fluorescence, luminescence, and absorption. As used herein, the terms "electromagnetic" or "electromagnetic wave" and "light" are used interchangeably. Electromagnetic waves of any frequency and wavelength that can be correlated to the amount of analyte bound to probe on the surface can be used in the present invention including gamma rays, x-rays, ultraviolet radiation, visible radiation, infrared radiation, and microwaves. While some embodiments are described with reference to visible (optical) light, the descriptions are not meant to limit the embodiments to those particular electromagnetic frequencies.

For the methods of the present invention it is desired that the signal changes upon the binding of the analyte to the probe in a manner that correlates with the amount of analyte bound. In some cases, the change in signal will be a change in intensity of the signal. In some embodiments, the signal intensity will increase as more analyte is bound to probe. In some embodiments, the signal intensity will decrease as more analyte is bound to probe. In some embodiments, the change in signal is not a change in intensity, but can be any other change in the signal that can be correlated with analyte binding to probe. For example, the change in signal upon binding of the probe can be a change in the frequency of the signal. In some embodiments, the signal frequency will increase as more analyte is bound to probe. In some embodiments, the signal frequency will decrease as more analyte is bound to the probe.

The signal that is measured is generally the signal in the region of the solid surface. In some embodiments, signal from moieties attached to the surface is used as the signal that can be correlated with the amount of analyte bound to the probe. In some embodiments signal from the solution is used as the signal that can be correlated with the amount of analyte bound to the probe.

In some embodiments of the methods of the present invention, labels are attached to the analytes and/or the probes. Any label can be used on the analyte or probe which can be useful in the correlation of signal with the amount of analyte bound to the probe. It would be understood by those of skill in the art that the type of label with is used on the analyte and/or probe will depend on the type of signal which is being used, for example, as described above, a dense label for a mechanical signal, or a redox active label for a voltammetric measurement.

In some embodiments, the signal that can be correlated to the amount of analyte bound to probe is due to the buildup of label at the surface as more analyte is bound to the probes on the surface. For example, where the analyte has a fluorescent label, as more analyte binds, the intensity of the fluorescent signal can increase in a manner that can be correlated with the amount of analyte bound to probe on the surface. In some embodiments, the signal that can be correlated to the amount of analyte bound to probe is due to the release of label from the surface. For example, where the probe has a fluorescent label and the label is released into solution upon the binding of the analyte to the probe, the fluorescent intensity at the surface will decrease as more analyte is bound and more fluorescent label is released.

In some embodiments, the signal that can be correlated to the amount of analyte bound to probe is due to a change in the signal from label on the surface upon binding of the analyte to the probe. For example, where a fluorescent label is on the surface, and the analyte is labeled with a compound capable of changing the fluorescent signal of the surface fluorescent label upon binding of the analyte with the probe, the change in signal can be correlated with the amount of analyte bound to probe. In some embodiments, the analyte is labeled with a quencher, and the decrease in intensity from the surface fluorescent label due to quenching is correlated to the increased amount of analyte bound to probe. In some embodiments, the analyte is labeled with a fluorescent compound which can undergo energy transfer with the fluorescent label on the surface such that the increase in fluorescence from the analyte fluorescent label and/or the decrease in fluorescence from the surface fluorescent label can be correlated with the amount of analyte bound to probe. In some embodiments the surface fluorescent label is bound directly, e.g. covalently to the probe. In some embodiments, the surface fluorescent label is bound to the surface, is not bound to the probe, but is in sufficient proximity that the binding of the analyte to the probe produces a change in signal from the surface fluorescent label that can be correlated with the amount of analyte bound to probe.

In some embodiments, the analyte is unlabeled, and the binding characteristics and or concentration of the analyte is determined by competitive binding with another labeled species, which competes with the analyte for biding to a probe. For example, where we have a solution with an analyte, A, whose concentration we want to determine, and we have a competitive binding species, B, whose binding characteristics with probe and whose concentration are known, then using the present invention, we can use, for example, an array of probes on a surface to determine the concentration of A by determining the amount of competitive binding of B to a probe. For example, the probe is attached to a surface that is fluorescently labeled, and B is labeled with a quencher such that the level of quenching of the surface fluorescence can be correlated with the amount of B bound to the probe. The rate of binding of B to the probe is measured in real time, and the concentration of A is determined by knowing the characteristics of A as a competitive binder. In some embodiments, the amount of the competitive binding species does not need to be known beforehand. For instance, the kinetics of binding of be can be measured in the fluid volume, then the conditions can be changed, (e.g. increasing the stringency) such that B is released from the probe, then the analyte A is added, and the binding of B under competition with A is measured. This example illustrates an advantage of the being able to change the conditions of the medium during one experiment. In some cases, A and B can be the same species, where B is labeled, and the amount of B is known, and the amount of A can be determined by the kinetics of the binding of B. In some cases, A and B are not the same species, but compete for binding with a probe: This competitive binding real-time assay can be done with all types of molecular species described herein including nucleic acids, antibodies, enzymes, binding proteins, carbohydrates and lipids.

Electromagnetic Signals—Optical Methods

The use of optical detection provides a variety of useful ways of implementing the methods of the present invention. Optical methods include, without limitation, absorption, luminescence, and fluorescence.

Some embodiments of the invention involve measuring light absorption, for example by dyes. Dyes can absorb light within a given wavelength range allowing for the measurement of concentration of molecules that carry that dye. In the present invention, dyes can be used as labels, either on the analyte or on the probe. The amount of dye can be correlated with the amount of analyte bound to the surface in order to determine binding kinetics. Dyes can be, for example, small organic or organometallic compounds that can be, for example, covalently bound to the analyte to label the analyte. Dyes which absorb in the ultraviolet, visible, infrared, and which absorb outside these ranges can be used in the present invention. Methods such as attenuated total reflectance (ATR), for example for infrared, can be used to increase the sensitivity of the surface measurement.

Some embodiments of the invention involve measuring light generated by luminescence. Luminescence broadly includes chemiluminescence, bioluminescence, phosphorescence, and fluorescence. In some embodiments, chemiluminescence, wherein photons of light are created by a chemical reaction such as oxidation, can be used. Chemiluminescent species useful in the invention include, without limitation, luminol, cyalume, TMAE (tetrakis(dimethylamino)ethylene), oxalyl chloride, pyrogallol (1,2,3-trihydroxibenzene), lucigenin. In some embodiments, bioluminescence is used. Where the luminescence is bioluminescence, creation of the excited state derives from an enzyme catalyzed reaction. Bioluminescence derives from the capacity of living organisms to emit visible light through a variety of chemiluminescent reaction systems. Bioluminescence generally include three major components: a luciferin, a luciferase and molecular oxygen. However other components may also be required in some reactions, including cations ($Ca^{++}$ and $Mg^{++}$) and cofactors (ATP, NAD(P)H). Luciferases are enzymes that catalyze the oxidation of a substrate, luciferin, and produce an unstable intermediate. Light is emitted when the unstable intermediate decays to its ground state, generating oxyluciferin. Any of the different unrelated types of luciferin can be used herein including those from phyla which use a luciferin, known as coelenterazine, which contains a ring formed by three amino acids (2 tyrosines, and a phenylalanine). Photoproteins from animals such as jellyfish can be used where the "photoprotein" of the luciferin/luciferase system emits light upon calcium binding. Other bioluminescent systems as described in U.S. Patent Application 2007/0065818, and including bioluminescence resonance energy transfer (BRET) as described in U.S. Patent Application 2007/0077609 can be used in the present invention.

Fluorescent Systems

A useful embodiment of the present invention involves the use of fluorescence. As used herein, fluorescence refers to the process wherein a molecule relaxes to its ground state from an electronically excited state by emission of a photon. As used herein, the term fluorescence also encompasses phosphorescence. For fluorescence, a molecule is promoted to an electronically excited state by generally by the absorption of ultraviolet, visible, or near infrared radiation. The excited molecule then decays back to the ground state, or to a lower-lying excited electronic state, by emission of light. An advantage of fluorescence for the methods of the invention is its high sensitivity. Fluorimetry may achieve limits of detection several orders of magnitude lower than for absorption. Limits of detection of $10^{-10}$ M or lower are possible for intensely fluorescent molecules; in favorable cases under stringently controlled conditions, the ultimate limit of detection (a single molecule) may be reached.

A wide variety of fluorescent molecules can be utilized in the present invention including small molecules, fluorescent proteins and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™CBQCA; ATTO-TAG™FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 Ca.sup.2+Dye; Calcium Green-2 Ca.sup.2+; Calcium Green-5N Ca.sup.2+; Calcium Green-C18 Ca.sup.2+; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10 GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; LeucophorWS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™488; Oregon Green™500; Oregon Green™514; Pacific Blue; Pararosaniline (Feulgen); PBFI; PE-CyS; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PL); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl-RodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

Some embodiments of the present invention include the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750. Some embodiments of the present invention include the Cy Dye fluorophore series (GE Healthcare), also covering a wide spectrum such as Cy3, Cy3B, Cy3.5, Cy5, Cy5.5, Cy7. Some embodiments of the present invention include the Oyster dye fluorophores (Denovo Biolabels) such as Oyster-500, -550, -556, 645, 650, 656. Some embodiments of the present invention include the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL. Some embodiments of the present invention include the ATTO fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740. Some embodiments of the present invention include CAL Fluor and Quasar dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670. Some embodiments of the present invention include quantum dots such as the EviTags (Evident Technologies) or quantum dots of the Qdot series (Invitrogen) such as the Qdot 525, Qdot565, Qdot585, Qdot605, Qdot655, Qdot705, Qdot 800. Some embodiments of the present invention include fluorescein, rhodamine, and/or phycoerythrin.

FRET and Quenching

In some embodiments of the invention, fluorescence resonance energy transfer is used to produce a signal that can be correlated with the binding of the analyte to the probe. FRET arises from the properties of certain fluorophores. In FRET, energy is passed non-radiatively over a distance of about 1-10 nanometers between a donor molecule, which is a fluorophore, and an acceptor molecule. The donor absorbs a photon and transfers this energy non-radiatively to the acceptor (Forster, 1949, Z. Naturforsch. A4: 321-327; Clegg, 1992, Methods Enzymol. 211: 353-388). When two fluorophores whose excitation and emission spectra overlap are in close proximity, excitation of one fluorophore will cause it to emit light at wavelengths that are absorbed by and that stimulate the second fluorophore, causing it in turn to fluoresce. The excited-state energy of the first (donor) fluorophore is transferred by a resonance induced dipole—dipole interaction to the neighboring second (acceptor) fluorophore. As a result, the excited state lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (up to 7 to 10 nanometers. The efficiency of energy transfer can falls off rapidly with the distance between the donor and acceptor molecules.

Molecules that can be used in FRET include the fluorophores described above, and includes fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In some embodiments of the methods of the present invention, the acceptor of the FRET pair is used to quench the fluorescence of the donor. In some cases, the acceptor has little to no fluorescence. The FRET acceptors that are useful for quenching are referred to as quenchers. Quenchers useful in the methods of the present invention include, without limitation, Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare), which can be used, for example, in conjunction with donor fluors such as Cy3B, Cy3, or Cy5; DY-Quenchers (Dyomics), such as DYQ-660 and DYQ-661; and ATTO fluorescent quenchers (ATTO-TEC GmbH), such as ATTO 540Q, 580Q, 612Q.

In some embodiments of the methods of the invention, both the analytes and the probes have labels that are members of a FRET pair, and the labels are attached such that when an analyte binds to a probe, FRET will occur between the labels, resulting in a change in signal that can be correlated with the binding of analyte to probe in real-time. The change in signal can be the decrease in the intensity of the donor and/or the increase in the intensity of the acceptor. The FRET pair can be chosen such that emission wavelength of the donor fluorophore is far enough from the emission wavelength of the acceptor fluorophore, that the signals can be independently measured. This allows the measurement of both the decrease in signal from the donor and the increase in signal from the acceptor at the same time, which can result in improvements in the quality of the measurement of binding. In some cases, the probe will have a label that is the donor of the donor-acceptor pair. In some cases, the analyte will have a label that is the donor of the donor acceptor pair.

In some embodiments of the methods of the invention, the analyte will have a fluorescent label that is a member of a FRET pair, and the other member of the FRET pair will be attached to the surface, wherein the member of the FRET pair attached to the surface is not covalently linked to the probe. In some cases, the analyte will have a label that is the donor of the donor-acceptor pair. In some cases, the analyte will have a label that is the acceptor of the donor acceptor pair. In some embodiments, the member of the FRET pair that is attached to the surface is attached to an oligonucleotide which is attached to the surface (a surface-bound label). The oligonucleotide that is labeled with the FRET pair can be a nucleotide sequence that does not have a sequence anticipated to specifically bind to an analyte. The use of a surface-bound label allows for the labeling of multiple areas of an array without having to label each specific binding probe. This can simplify the production of the array and reduce costs. We have found that even though the surface-bound FRET pairs are not covalently bound to the probe, they can be sensitive to the binding of the analyte labeled with the other member of the FRET pair in a manner that allows the change in signal to be correlated with the amount of analyte bound to probe.

In some embodiments of the methods of the present invention, the analyte is labeled with a quencher, and the probe is labeled with a donor fluorophore. The analyte is labeled with the quencher such that when analyte binds with the probe, the fluorescence from the fluorescent label on the probe is quenched. Thus, the signal, measured in real-time, can be correlated with the amount of binding of the analyte and the probe, allowing for the measurement of the kinetics of the binding. In some embodiments of the methods of the present invention, the analyte is labeled with a quencher, and the probe is labeled with a donor fluorophore, that is not covalently attached to it. The quencher is labeled such that when analyte binds with the probe, the fluorescence from the fluorescent label on the probe is quenched. Thus, the signal, measured in real-time, can be correlated with the amount of binding of the analyte and the probe, allowing for the measurement of the kinetics of the binding.

In some embodiments of the methods of the present invention, the analyte is labeled with a quencher, and the surface is labeled with a donor fluorophore wherein the donor fluorophore is not covalently linked to the probe (e.g. with a surface bound fluorescent label). The quencher is labeled such that when analyte binds with the probe, the fluorescence from the fluorescent label on the surface is quenched. Thus, the signal, measured in real-time, can be correlated with the amount of binding of the analyte and the probe, allowing for the measurement of the kinetics of the binding.

Where the probe is labeled with a fluorophore, one aspect of the invention is the use of an image of the fluorescently labeled probe on the surface obtained before binding has occurred in order to effectively establish a baseline signal for the state where no binding of analyte to probe has occurred. In conventional arrays, in which unlabeled probe is treated with labeled analyte, and the signal is measured after hybridization and washing, it can be difficult to know exactly how much probe is actually on the array in the region of interest. Thus, differences in array manufacture can affect the quality of the data. In the present invention, where the probe is labeled with fluorophore, the image of the labeled probe on the surface provides a measurement of the amount of probe actually on the surface, increasing the quality and reliability of the binding measurement.

Figure 5:
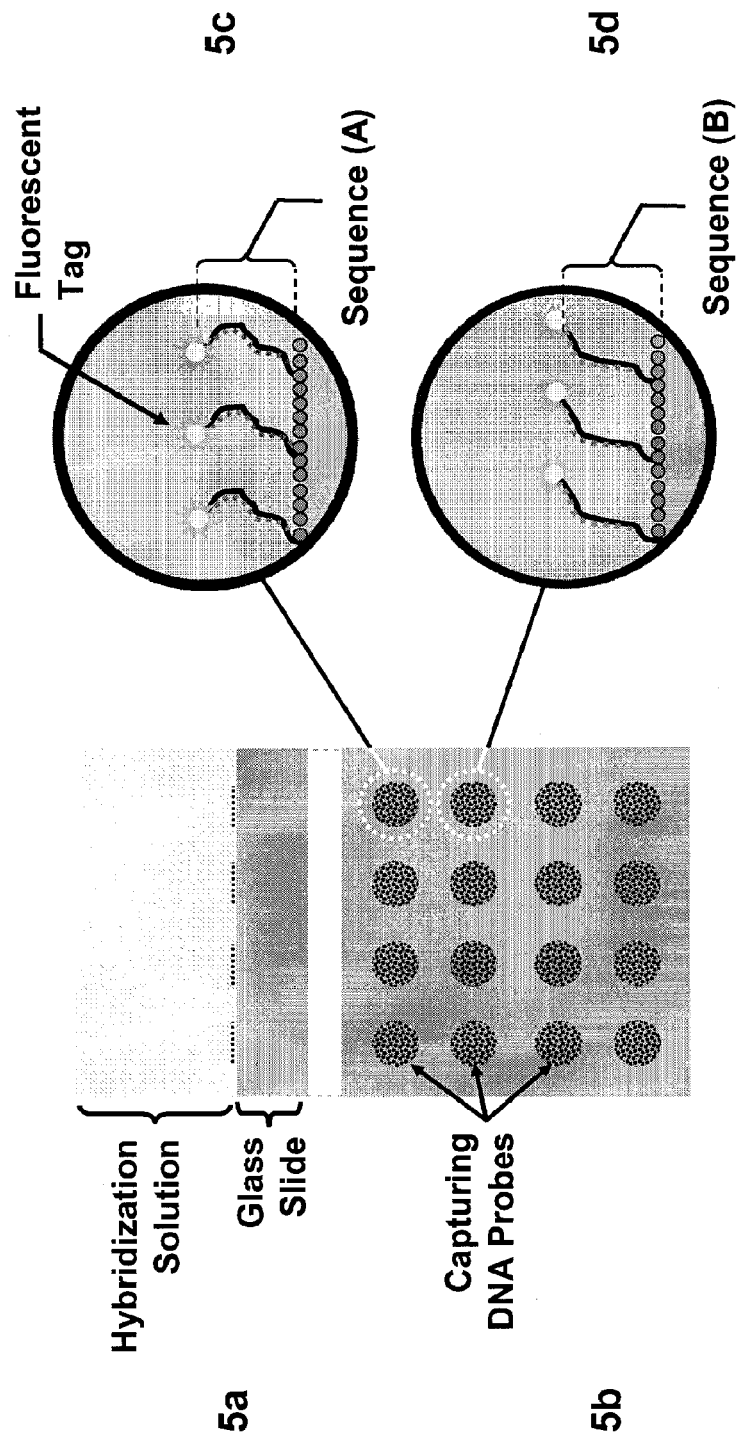
FIG. 5 shows a nucleic acid based real-time microarray system of the present invention where the probes are labeled with fluorescent moieties.
Figure 6:
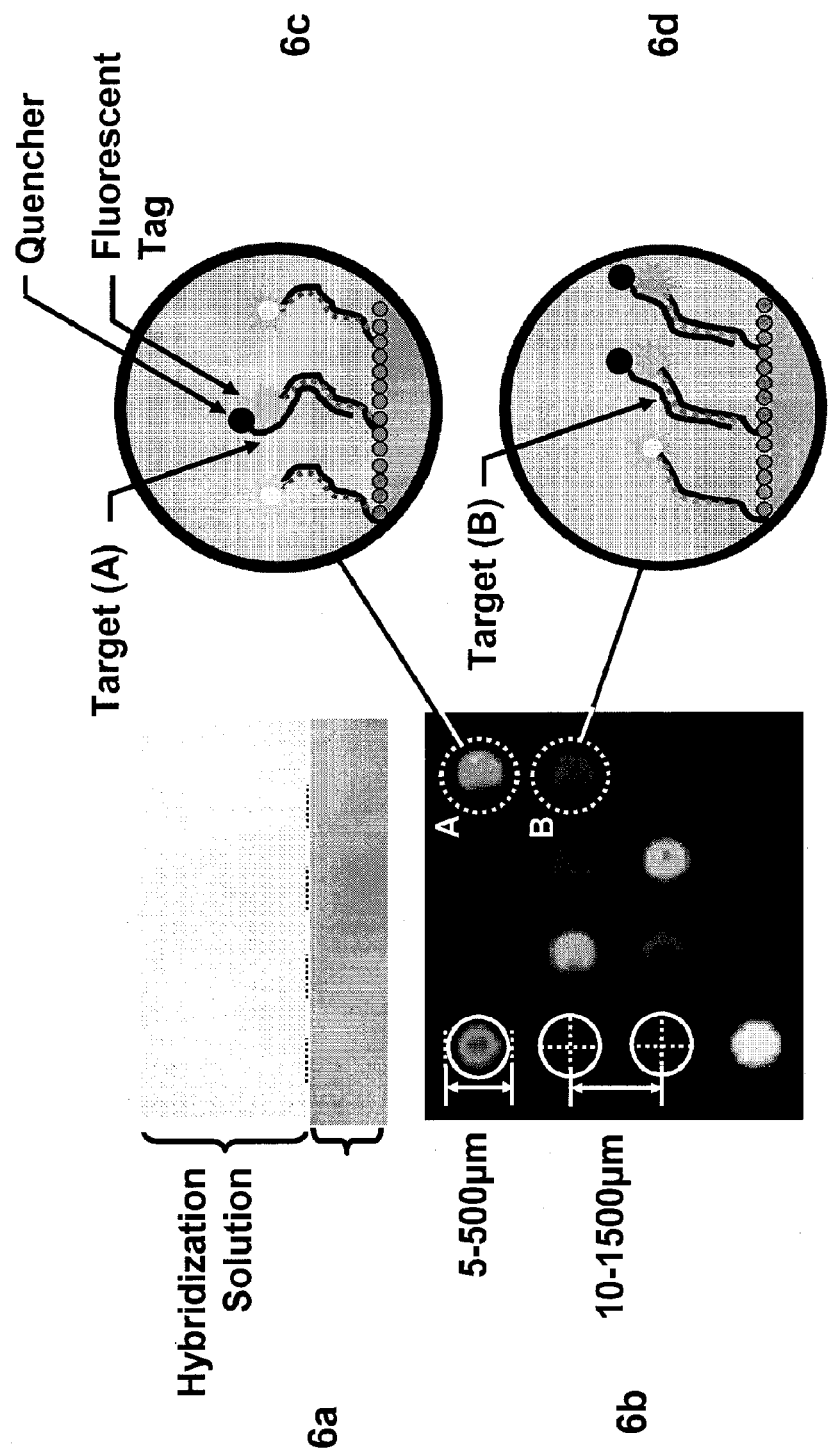
FIG. 6a-d shows a nucleic acid based real-time microarray system of the present invention where the probes are labeled with fluorescent moieties, the analytes are labeled with quenchers, and the fluorescent intensity on various spots can be used to measure the amount of analyte specifically bound to probe.

One exemplary embodiment of the method of the invention is illustrated in FIGS. 5 and 6. FIG. 5B shows a top view of a 4 by 4 microarray that has 16 independently addressable spots, each spot having bound DNA probes, wherein the probes are labeled with fluorescent label. FIG. 5C shows a close up view of one of the spots illustrating the attached probe of sequence (A), each probe having a fluorescent label. FIG. 5D shows the close up view of a second spot with attached probes of sequence (B), each probe having a fluorescent label. FIG. 5A shows a side view of the array, showing that the array is in contact with the hybridization solution. FIG. 5 represents a time at which no analyte is bound to probe on the array.

FIG. 6 illustrates the same array as in FIG. 5 after hybridization for some time with target analytes (targets) having a quencher attached. FIGS. 6A and 6B shows a side view and top view of the array, still in contact with the hybridization solution. The different spots on the array in FIG. 6B have different light intensities, indicating that there is a different amount of binding of analyte at each spot, and therefore a different amount of fluorescence from the spots. FIG. 6C shows a close up view illustrating that a small amount of target (A) has specifically bound (hybridized) to probe (A) resulting in quenching of each molecule of probe to which analyte is bound. FIG. 6D illustrates that a larger amount of analyte (B) has specifically bound (hybridized) to probe (B), resulting in a higher level of quenching than observed for spot (A). The signal from each of the spots on the array can be measured at various time points during the binding reaction between analytes and probes, while the solution containing the analyte is in contact with the solid surface of the microarray, allowing a real-time measurement of the amount of analyte-probe binding, and allowing the measurement of binding kinetics at each spot.

Measuring Cross-Hybridization

One aspect of the methods of the present invention is the step of performing an algorithm on real-time binding data to determine cross-hybridization for multiple probes on a substrate. One embodiment involves improving the quality of analyte-probe binding measurements by determining and correcting for cross-hybridization.

In its early stages, the probe-target binding kinetics can be described by a simple first-order differential equation whose time-domain solution is given by an exponential function; the rate of decay of the exponential function is determined by the binding reaction rate. Non-specific binding can have an adverse effect on the accuracy of microarray platforms, especially if the amount of the non-specific target is high relative to the specific target. One reason is that the specific and non-specific targets will compete for the same probe, and even though the probability of non-specific binding is much lower it may have an effect if the amount of the non-specific target is much higher. Fortunately, specific and non-specific bindings have different reaction rates, by virtue of the fact that the binding probabilities and target amounts are different; therefore, if both specific and non-specific (i.e., interfering) targets bind to a probe on a microarray or a parallel affinity-based biosensor, the signal measured by a RT-μArray system can be represented by a sum of exponentials, $$\mu(t) = \Sigma \alpha_j exp(\beta_j t), \quad (1)$$

where $\Sigma \alpha_j$ gives the initial intensity of the probe spots, the $\beta_j$ are the rates of decay for the specific (j=1) and non-specific (j=2, 3, ...) bindings, and where the $\alpha_j$ themselves depend on the reaction rates and target densities. In certain embodiments of the invention, we employ the so-called Prony method or one of its modifications. This method essentially represents the signal $\mu(t)$ in terms of the coefficients of the original differential equation. These coefficients are computed by finding eigenvalues of an appropriate covariance matrix. In other embodiments of the invention, algebraic characterization using singular value decomposition of the correlation matrix of the data is employed. In yet another embodiment of the invention, information-theoretic or Bayesian techniques can be used to detect a presence of the species that bind non-specifically, estimate the number of such species, and quantify their amounts.

The Basic Algorithm

The hybridization process in general satisfies a nonlinear differential equation. To see this, let p(t) denote the number of available probe molecules at a given spot at time t, and let n(t) denote the number of analytes in the solution that are specific to this spot. Thus, if the probability that an analyte be in close proximity to a probe molecule is $P_{near}$, the probability that it binds to the probe once it is near in a unit interval of time is $P_h$, and the probability that an analyte bound to a probe molecule is released in a unit interval of time is $P_r$, then we may write $$p(t+\delta)-p(t)=\delta(p_0-p(t))P_r-\delta p(t)n(t)P_{near}P_h, \quad (1)$$

where $p_0$ denotes the initial number of probe molecules on this probe spot of the array. If we denote the total number of analyte molecules by N then it is clear that $n(t)=N-p_0+p(t)$. Letting $\delta \to 0$, therefore gives $$\frac{dp(t)}{dt} = (p_0 - p(t))P_r - p(t)(N - p_0 + p(t))P_{near}P_h. \quad (2)$$

Upon rearranging terms, we have $$\frac{dp(t)}{dt} = p_0 P_r - p(t)[P_r + (N - p_0)P_{near}P_h] - p^2(t)P_{near}P_h, \quad (3)$$

which is the nonlinear equation we were seeking. This is a Riccati equation and can be solved in closed form (however, we shall not do so here). In any event, it is clear that by looking at the trajectory of p(t) one can glean information about the parameters N, $p_0$, $P_h$, $P_r$. For example, the steady-state of p(t), i.e., $p_\infty = p(\infty)$, satisfies the quadratic equation $$P_{near}P_h p_\infty^2 + [P_r + (N-p_0)P_{near}P_h]p_\infty - p_0 P_r = 0 \quad (4)$$

and so measuring it, gives us information about the parameters of interest.

Determining the Analyte Concentration

The equations are often more instructive when written in terms of the number of probe molecules that have bound to analytes, i.e., $q(t)=_0-p(t)$. In this case we may write $$-\frac{dq(t)}{dt} = q(t)P_r - (p_0 - q(t))(N - q(t))P_{near}P_h, \quad (5)$$

which upon a rearrangement of terms becomes $$\frac{dq(t)}{dt} = Np_0 P_{near}P_h - [P_r + (N + p_0)P_{near}P_h]q(t) + P_{near}P_h q^2(t). \quad (6)$$

In the early phase of the hybridization process, i.e., when q(t) is very small, we may ignore the quadratic term in the differential equation and write $$\frac{dq(t)}{dt} \approx Np_0 P_{near}P_h - [P_r + (N + p_0)P_{near}P_h]q(t). \quad (7)$$

This has the solution $$q(t) \approx \frac{Np_0 P_{near}P_h}{P_r + (N + p_0)P_{near}P_h}(1 - \exp(-t[P_r + (N + p_0)P_{near}P_h])). \quad (8)$$

The above formula has several different ramifications; first the slope of increase of q(t), equivalently, the slope of decay of p(t), is given by $$\left.\frac{dq(t)}{dt}\right|_{t=0} = Np_0 P_{near}P_h, \quad (9)$$

which is proportional to the number of analytes in the solution, N.

Second, the reaction rate also has information on the number of analytes. In fact, the reaction rate is simply the coefficient of t in the exponential function for q(t), which is readily seen to be $$\text{reaction\_rate} = P_r + (N+p_0)P_{near}P_h. \quad (10)$$

Though this is not quite a linear relationship for N, it can still be used to estimate the number of analytes.

Of course, one can estimate N jointly from both the initial slope and the reaction rate. In particular, it is often true that $P_r$ is very small and can be ignored compared to other terms. Therefore we shall take $$\text{reaction\_rate} = (N+p_0)P_{near}P_h \quad (11)$$

Determining and Suppressing Cross-Hybridization

The other advantage of looking at the reaction rate is that it allows for one to deal with cross-hybridization and to suppress its effect. As mentioned earlier, in the early phase of the hybridization process, the number of available probe molecules, or equivalently the light intensity of a probe spot, decays exponentially with time. For example $$C_k \exp(-r_k t), \quad (12)$$

where $C_k$ is a constant and $r_k$ is the reaction rate that can be determined from the parameters of the experiment (probability of hybridization, number of analytes, number of probe molecules, etc.). In particular, as seen from (11), $r_k$ is linear in the number of target analytes, $N_k$, say.

If, in addition to hybridization of the target of interest, a number of other targets cross-hybridize to the same probe spot, the light intensity of the probe spot will decay as the sum of several exponentials, i.e., $$I(t) = \sum_{k=0}^{K-1} C_k \exp(-r_k t), \quad (13)$$

where k=0 corresponds to the desired target and k=1, ..., K−1 corresponds to the K−1 cross-hybridizing analytes. The whole point is that the reaction rates for the different analytes differ (due to different numbers of analytes, binding probabilities, etc.) so that if we can estimate the reaction rates from (13), we should be able to determine the number of molecules for each different analyte.

The RT-uArray system samples the signal (i.e., the light intensity) of the probe spots at certain time intervals (multiples of $\Delta$, say) and thus obtains the sequence $$y_n = I(n\Delta) + v(n\Delta) = \sum_{k=0}^{K-1} C_k \exp(-n\Delta r_k) + v(n\Delta) \quad (14)$$

for n=0, 1, ... T−1, where T is the total number of samples and v(t) represents the measurement noise. Defining $u_k = \exp(-\Delta r_k)$ we may write $$y_n = \sum_{k=0}^{K-1} C_k u_k^n + v_n. \quad (15)$$

The goal is to (i) determine the value of K (i.e., how many analytes are binding to the probe spot), (ii) to estimate the values of the pairs $\{C_k, u_k\}$ for all k=1, ..., K−1 and (iii) to determine the number of each analyte $N_k$ (recall from (9) that $C_k$ is proportional to the number of analytes and that from (11) the reaction rate is linear in $N_k$).

The problem of determining the number of exponential signals in noisy measurements, and estimating the individual rates, is a classical one in signal processing and is generally referred to as system identification. (There are a multitude of books and papers on this subject.) The basic idea is that, when $y_n$ is the sum of K exponentials, it satisfies a K th order recurrence equation $$y_n + h_1 y_{n-1} + \ldots + h_{K-1} y_{n-K+1} + h_K y_{n-K} = 0 \quad (16)$$

Furthermore, the $u_k$ are the roots of the polynomial $$H(z) = z^K + h_1 z^{Kn-} \ldots + h_{K-1} z + h_k \quad (17)$$

In practice, since one observes a noisy signal, one first uses the measurements to form the so-called Hankel matrix $$\begin{pmatrix} y_{T/2} & y_{T/2-1} & \cdots & y_1 & y_0 \\ y_{T/2+1} & y_{T/2} & \cdots & y_2 & y_1 \\ \vdots & \vdots & \ddots & \vdots & \vdots \\ y_T & y_{T-1} & \cdots & y_{T/2+1} & y_{T/2} \end{pmatrix} \quad (18)$$

When $y_n$ is the sum of K exponentials, the above Hankel matrix has rank K, i.e., only K nonzero eigenvalues. When $y_n$ is noisy, the standard practice is to compute the singular values of the Hankel matrix and estimate K as being the number of significant singular values.

Once K has been determined, one forms the (T−K+1)×(K+1) Hankel matrix $$\begin{pmatrix} y_K & y_{K-1} & \cdots & y_1 & y_0 \\ y_{K+1} & y_K & \cdots & y_2 & y_1 \\ \vdots & \vdots & \ddots & \vdots & \vdots \\ y_T & y_{T-1} & \cdots & y_{T-K+1} & y_{T-K} \end{pmatrix} \quad (19)$$

and then identifies the vector $(1\ h_1 \ldots h_k)^t$ with the smallest right singular vector of (19).

As mentioned earlier, the roots of H(z) are the desired $u_k$, from which we determine the rates $r_k$ and thereby the amounts of targets present. While the algorithm outlined above can be used, a variety of different techniques to find the $u_k$, including, but not limited to, total least squares, ESPRIT, Prony's method, may be used.

In addition to the algorithm described above, other algorithmic solutions can be used, including the methods overviewed in (Petersson et al., Applied Mathematics and Computation, vol. 126, no. 1, February 2002, pp. 31-61). The methods described above provide the ability to quantify the amounts of the species that bind whether specifically or non-specifically.

Arrays

One aspect of the invention is an array that has a solid surface with a plurality of probes attached to it, where the array can be used for the real-time measurement of binding of analyte to the plurality of probes.

The arrays of the present invention comprise probes attached to a solid substrate. The solid substrate may be biological, nonbiological, organic, inorganic, or a combination of any of these, existing as particles, strands, precipitates, gels, sheets, tubing, spheres, containers, capillaries, pads, slices, films, plates, slides, semiconductor integrated chips, etc. The solid substrate is preferably flat but may take on alternative surface configurations. For example, the solid substrate may contain raised or depressed regions on which synthesis or deposition takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof.

The substrate can be a homogeneous solid and/or unmoving mass much larger than the capturing probe where the capturing probes are confined and/or immobilized within a certain distance of it. The mass of the substrate is generally at least 100 times larger than capturing probes mass. In certain embodiments, the surface of the substrate is planar with roughness of 0.1 nm to 100 nm, but typically between 1 nm to 10 nm. In other embodiments the substrate can be a porous surface with roughness of larger than 100 nm. In other embodiments, the surface of the substrate can be non-planar. Examples of non-planar substrates are spherical magnetic beads, spherical glass beads, and solid metal and/or semiconductor and/or dielectric particles.

In some embodiments the substrate is optically clear, allowing light to be transmitted through the substrate, and allowing excitation and or detection to occur from light passing through the substrate. In some embodiments the substrate is opaque. In some embodiments, the substrate is reflective, allowing for light to pass through the surface layer containing probes and reflect back to a detector.

In some embodiments, glass slides are used to prepare biochips. The substrates (such as films or membranes) can also be made of silica, silicon, plastic, metal, metal-alloy, anopore, polymeric, and nylon. The surfaces of substrates can be treated with a layer of chemicals prior to attaching probes to enhance the binding or to inhibit non-specific binding during use. For example, glass slides can be coated with self-assembled monolayer (SAM) coatings, such as coatings of as aminoalkyl silanes, or of polymeric materials, such as acrylamide and proteins. A variety of commercially available slides can be used. Some examples of such slides include, but are not limited to, 3D-link® (Surmodics), EZ-Rays® (Mosaic Technologies), Fastslides® (Schleicher and Schuell), Superaldehyde®, and Superamine® (CEL Technologies).

Probes can be attached covalently to the solid surface of the substrate (but non-covalent attachment methods can also be used). In one embodiment, similar substrate, coating, and attachment chemistries are used for all three—UniScreen™, ProScreen™, NuScreen™—devices. In another embodiment, different chemistries are applied.

A number of different chemical surface modifiers can be added to substrates to attach the probes to the substrates. Examples of chemical surface modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. Glass slides with such chemically modified surfaces are commercially available for a number of modifications. These can easily be prepared for the rest, using standard methods (Microarray Biochip Technologies, Mark Schena, Editor, March 2000, Biotechniques Books).

In one embodiment, substrate surfaces reactive towards amines are used. An advantage of this reaction is that it is fast, with no toxic by-products. Examples of such surfaces include NHS-esters, aldehyde, epoxide, acyl halide, and thio-ester. Most proteins, peptides, glycopeptides, etc. have free amine groups, which will react with such surfaces to link them covalently to these surfaces. Nucleic acid probes with internal or terminal amine groups can also be synthesized, and are commercially available (e.g., from IDT or Operon). Thus, nucleic acids can be bound (e.g., covalently or non-covalently) to surfaces using similar chemistries.

The substrate surfaces need not be reactive towards amines, but many substrate surfaces can be easily converted into amine-reactive substrates with coatings. Examples of coatings include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), and BSA coatings (which can be reacted with bis-NHS cross-linkers, maleimide-NHS cross-linkers, etc.). Alternatively, the probes, rather than the substrate, can be reacted with specific chemical modifiers to make them reactive to the respective surfaces.

A number of other multi-functional cross-linking agents can be used to convert the chemical reactivity of one kind of surface to another. These groups can be bifunctional, tri-functional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS-Y-NHS, is a homo-bi-functional cross-linker and would connect an amine surface with an amine-group containing molecule. If X is NHS-ester and Z is a maleimide group, the resulting cross-linker, NHS-Y-maleimide, is a hetero-bi-functional cross-linker and would link an amine surface (or a thiol surface) with a thio-group (or amino-group) containing probe. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc. Such cross-linkers can be reacted with the surface or with the probes or with both, in order to conjugate a probe to a surface.

Other alternatives include thiol reactive surfaces such as acrydite, maleimide, acyl halide and thio-ester surfaces. Such surfaces can covalently link proteins, peptides, glycopeptides, etc., via a (usually present) thiol group. Nucleic acid probes containing pendant thiol-groups can also be easily synthesized.

Alternatively, one can modify glass surfaces with molecules such as polyethylene glycol (PEG), e.g. PEGs of mixed lengths Other surface modification alternatives (such as photo-crosslinkable surfaces and thermally cross-linkable surfaces) are known to those skilled in the art. Some technologies are commercially available, such as those from Mosiac Technologies (Waltham, Mass.), Exiqon™ (Vedbaek, Denmark), Schleicher and Schuell (Keene, N.H.), Surmodics™ (St. Paul, Minn.), Xenopore™ (Hawthorne, N.J.), Pamgene (Netherlands), Eppendorf (Germany), Prolinx (Bothell, Wash.), Spectral Genomics (Houston, Tex.), and Combimatrix™ (Bothell, Wash.).

Surfaces other than glass are also suitable for such devices. For example, metallic surfaces, such as gold, silicon, copper, titanium, and aluminum, metal oxides, such as silicon oxide, titanium oxide, and iron oxide, and plastics, such as polystyrene, and polyethylene, zeolites, and other materials can also be used. The devices can also be prepared on LED (Light Emitting Diode) and OLED (Organic Light Emitting Diode) surfaces. An array of LEDs or OLEDs can be used at the base of a probe array. An advantage of such systems is that they provide easy optoelectronic means of result readout. In some cases, the results can be read-out using a naked eye.

Probes can be deposited onto the substrates, e.g., onto a modified surface, using either contact-mode printing methods using solid pins, quill-pins, ink-jet systems, ring-and-pin systems, etc. (see, e.g., U.S. Pat. Nos. 6,083,763 and 6,110,426) or non-contact printing methods (using piezoelectric, bubble-jet, syringe, electro-kinetic, mechanical, or acoustic methods. Devices to deposit and distribute probes onto substrate surfaces are produced by, e.g., Packard Instruments. There are many other methods known in the art. Preferred devices for depositing, e.g., spotting, probes onto substrates include solid pins or quill pins (Telechem/Biorobotics).

The arrays of the present invention can also be three-dimensional arrays such as porous arrays. Such as devices consisting of one or more porous gel-bound probes in an array or an array of arrays format. A device can have one or more such structures and the structures can be of any geometric shape and form. The structures can also be vertically straight, angled, or twisted. Thus, each device denotes a (multiplexed) reaction site. The device can be used to perform reactions simultaneously or sequentially. Any of the known substrates and chemistries can be used to create such a device. For example, glass, silica, silicon wafers, plastic, metals; and metal alloys can all be used as the solid support (see. e.g., Stillman B A, Tonkinson J L, Scleicher and Schuell; Biotechniques, 29(3), 630-635, 2000; Rehmna et. al; Mosaic Technologies Inc., Nucleic Acids Research, 27(2), 649-655, 1999). In other embodiments, the intermediate species can be immobilized to the substrate using mechanical and/or electrostatic and/or and magnetic forces. Examples are magnetic beads with magnetic fields and glass beads with electrostatic fields. Bead based methods are described, for example in Gunderson et al., Genome Research, 870-877, 2004; Michael et al., Anal. Chem. 70, 1242-1248, 1998; Han et al., Nat. Biotechnol, 19, 631-635, 2001; and Lockhart et al., Nat. Biotechnol. 19, 1122-1123, 2001.

In other embodiments, the microarrays are manufactured through the in-situ synthesis of the probes. This in-situ synthesis can be achieved using phosphoramidite chemistry and/or combinatorial chemistry. In some cases, the deprotection steps are performed by photodeprotection (such as the Maskless Array Synthesizer (MAS) technology, (NimbleGen; or the photolithographic process, by Affymetrix). In other cases, deprotection can be achieved electrochemically (such as in the Combimatrix procedure). Microarrays for the present invention can also be manufactured by using the inkjet technology (Agilent).

For the arrays of the present invention, the plurality of probes may be located in one addressable region and/or in multiple addressable regions on the solid substrate. In some embodiments the solid substrate has about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 addressable regions with probes.

The spots may range in size from about 1 nm to 10 nm, in some embodiments from about 1 to 1000 micron and more in some embodiments from about 5 to 100 micron. The density of the spots may also vary, where the density is generally at in some embodiments about 1 spot/cm$^2$, in some embodiments at least about 100 spots/cm$^2$ and in other embodiments at least about 400 spots/cm$^2$, where the density may be as high as $10^6$ spots/cm$^2$ or higher.

The shape of the spots can be square, round, oval or any other arbitrary shape.

One aspect of the invention is an array that comprises a solid substrate having a surface and a plurality of different probes, wherein (a) the different probes are immobilized to the surface at different addressable locations, (b) the addressable locations comprise optical signal moieties bound to the surface, (c) the optical signal moieties are not bound directly to the probes, and (d) the optical signal from the optical signal moieties is capable of changing upon binding of an analyte to the probes. For these arrays, the optical signal moiety, for example, a fluorescent moeity is bound directly to the surface, but is not covalently bound to a probe, and in these cases the probe need not be labeled. The fluorescent moiety can be bound to the surface or synthesized in-situ by an of the methods described above for probes. The fluorescent moiety can be attached to an oligonucleotide that is not a probe, for example, having a sequence that is not complementary to target analytes in solution.

In one embodiment, a fluorescent moiety on the surface (surface-bound label) can be brought to the proximity of the probe via post-probe-synthesis or post-probe-deposition methods.

In some embodiments, the label can be bound to the probe by non-covalent means, such as by hybridization. For example, in certain embodiments of the present invention, some or all of the probes on the microarray may contain two different sequence segments: one segment that consists of a sequence that is specific to the probe and specific for the detection of a given target analyte, and another segment that is a sequence that is common to all or many of the probes on the microarray. These two sequence segments can be immediately adjacent to each other on the probe, or separated by a linker. In this embodiment, the microarray is first hybridized with a (labeled oligonucleotide that is complementary to the common sequence segment, thus resulting in a microarray in which the spots or features where the probes are located also now contain fluorescent labels. These non-covalently bound labels can be bound to the probe such that FRET and or quenching of the label occurs upon binding of an analyte to the specific portion of the probe. This method can be advantageous, for instance by (1) lowering the cost of manufacturing microarrays that can be used in the real-time platform and/or (2) enabling the use of in-situ synthesized arrays in the real time platform. The labeled oligonucleotide can be a locked nucleic acid (LNA) oligonucleotide. LNA oligonucleotides can be useful because the LNA modification can result in enhanced hybridization properties (for example, diminishing the sequence length that is needed to achieve a certain Tm) (Jepsen et al., Oligonucleotides. 2004; 14(2):130-46).

Systems

One aspect of the invention is a system comprising:(a) a device with (i) a solid support having a surface and (ii) a plurality of different probes, wherein the different probes are immobilized to the surface; (b) a fluid volume comprising an analyte wherein the fluid volume is in contact with the solid support, and (c) a detector assembly comprising means to detect signals measured at multiple time points from each of a plurality of spots on the microarray while the fluid volume is in contact with the solid support.

The fluid volume can be introduced and held in the system by any method that will maintain the fluid in contact with the solid support. In many cases the fluid is held in a chamber. In some embodiments the chamber is open on one face, in other embodiments the chamber will mostly enclose the fluid. In some embodiments, the chamber will have one or more ports for introducing and/or removing material (usually fluids) from the chamber. In some embodiments one side of the chamber comprises the solid substrate on which the probes are attached. In some embodiments the chamber is integral to the solid substrate. In some embodiments, the chamber is a sub-assembly to which the solid substrate with probes can be removably attached. In some embodiments, some or all of the fluid chamber is an integral part of the instrument that comprises the detector. The chamber can be designed such that the signal that can be correlated with analyte-probe binding can be detected by a detector outside of the chamber. For instance, all or a portion of the chamber can be transparent to light to allow light in or out of the chamber to facilitate excitation and detection of fluorophores.

The detector assembly can comprise a single detector or an array of detectors or transducers. As used herein, the terms detector and transducer are used interchangeably, and refer to a component that is capable of detecting a signal that can be correlated with the amount of analyte-probe binding. Where the detector system is an array of transducers, in some embodiments, the detector system is a fixed array of transducers, wherein one or more transducers in the transducer array corresponds to one independently addressable area of the array. In some embodiments, the detector or the array of transducers scans the array such that a given detector or transducer element detects signals from different addressable areas of the array during a binding reaction.

In some embodiments the detector array is in contact with the solid substrate. In some embodiments, the detector is at a distance away from the substrate. Where the detector is a distance away from the substrate, in some embodiments, the detector or detector array is capable of scanning the substrate in order to measure signal from multiple addressable areas. In some embodiments, the detector is an optical detector which is optically coupled to the substrate. The detector can be optically coupled to the substrate, for example with one or more lenses or waveguides.

Figure 9:
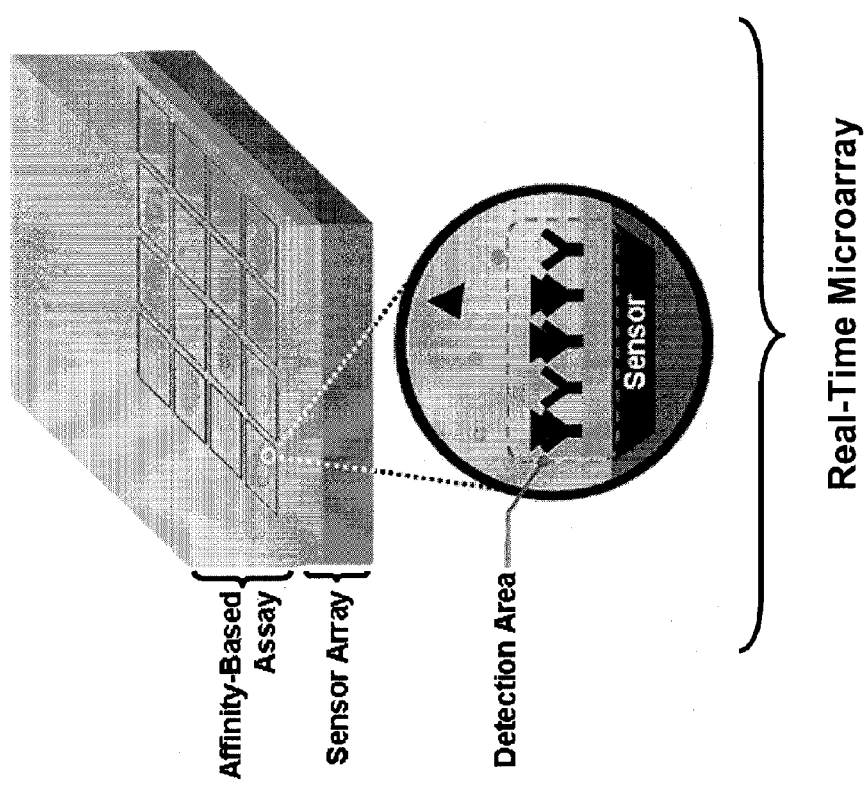
FIG. 9 shows a real-time microarray system where the detection system comprises a sensor array in intimate proximity of the capturing spots.

FIG. 9 shows an example of a real-time microarray system where the detection system comprises a sensor array in intimate proximity of the capturing spots. In this embodiment, individual sensors detect the binding events of a single capturing spots.

In some embodiments, the detector is optically coupled through spatially confined excitation. This method is useful to optically couple the substrate to detector for a small region of substrate with probes. This method generally requires only a single detector, since only one region can create signal at a time. The method can be used in scanning systems, and is applicable in assays which an excitation is required for detection, such as fluorescence spectroscopy or surface plasmon resonance (SPR) methods.

In some embodiments, the detector is optically coupled through imaging using focal plane detector arrays: In this method the signal generated from the system is focused on a focal point detector array. This approach useful for optical detection systems where signal focusing can be carried out using lenses and other optical apparatus. Examples of detectors in these embodiments are complementary metal oxide semiconductor (CMOS) and charge coupled device (CCD) image sensors.

In some embodiments, the detector is optically coupled through surface imaging: In this method the detectors are placed in intimate proximity of the capturing probes such that the signal generated from the capturing region can only be observed by the dedicated detector. If a microarray with multiple capturing spots is used, multiple detectors are used, each dedicated to an individual spot. This method can be used in electrochemical-, optical-, and magnetic-based biosensors.

In some embodiments, the detector is optically coupled through surface imaging using signal couplers: In this method the detectors are not place in proximity of the capturing spots, however a signal coupler is used to direct signal from the capturing region to a detector. This method is generally used in optical detection systems where the signal coupling elements is a plurality of optical waveguide. Examples of signal coupling elements include fiber optic cables, fiber optic bundles, fiber optic faceplates, and light pipes.

The detectors of the present invention must be capable of capturing signal at multiple time points in real time, during the binding reaction. In some embodiments the detector is capable of measuring at least two signals in less than about 1 psec, 5 psec, 0.01 nsec, 0.05 nsec, 0.1 nsec, 0.5 nsec, 1 nsec, 5 nsec, 0.01 μsec, 0.05 μsec, 0.1 μsec, 0.5 μsec, 1 μsec, 5 μsec, 0.01 msec, 0.05 msec, 0.1 msec, 0.5 msec, 1 msec, 5 msec, 10 msec, 50 msec, 100 msec, 0.5 sec, 1 sec, 5 sec, 10 sec, or 60 sec.

In some embodiments the detector detects the signal at the substrate. In some embodiments the detector will detect the signal in the solution. In some embodiments, the detector will detect signal in both the solution and at the substrate.

In some embodiments the detector system is capable of detecting electrical, electrochemical, magnetic, mechanical, acoustic, or electromagnetic (light) signals.

Where the detector is capable of detecting optical signals, the detector can be, for example a photomultiplier tube (PMT), a CMOS sensor, or a (CCD) sensor. In some embodiments, the detector comprises a fiber-optic sensor.

In some embodiments, the system comprising the detector is capable of sensitive fluorescent measurements including synchronous fluorimetry, polarized fluorescent measurements, laser induced fluorescence, fluorescence decay, and time resolved fluorescence.

In some embodiments, the system comprises a light source, for example, for excitation of fluorescence. The light source is generally optically coupled to the substrate, for example with one or more lenses or waveguides. The light source can provide a single wavelength, e.g. a laser, or a band of wavelengths.

Figure 7:
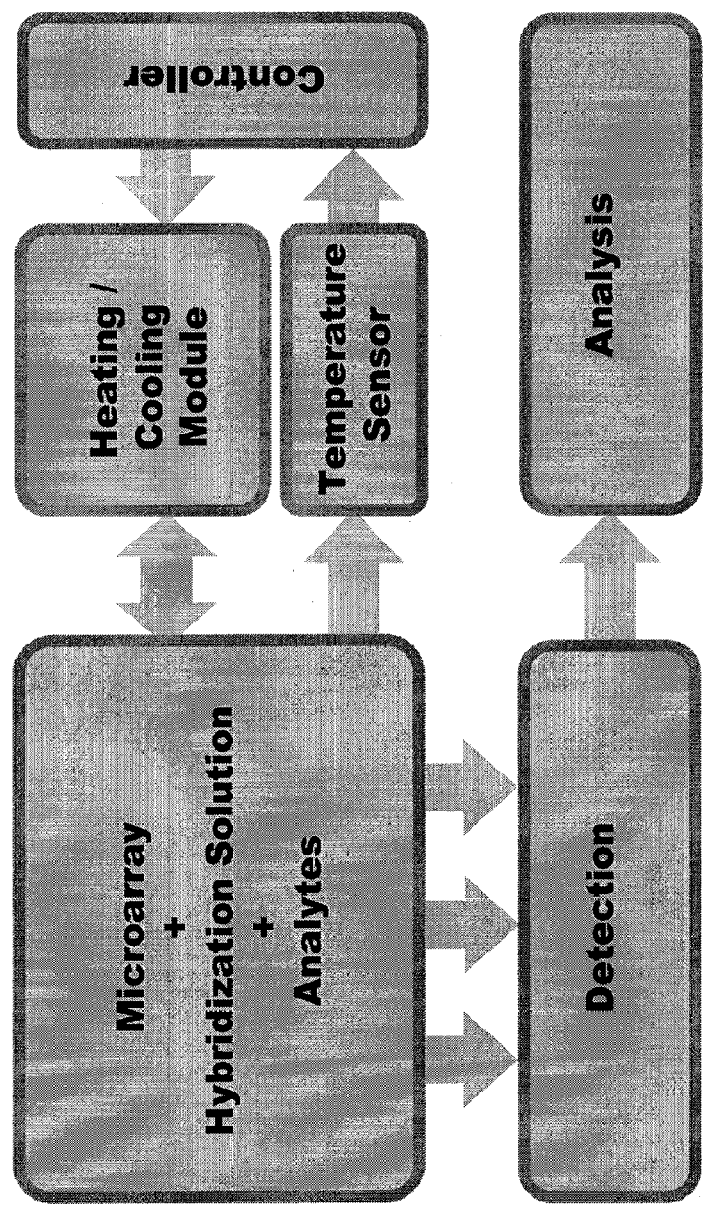
FIG. 7 shows a block diagram of a real-time microarray system of the present invention.

FIG. 7 shows a block diagram of the components of systems of the present invention. The system comprises of (i) reaction chamber which includes the microarray substrate, probes, analytes, and solution, (ii) heating and cooling modules and temperature sensor, (iii) temperature controller, and (iv) detector which is connected to an analysis block, where the latter is a part of a computing system.

Figure 8:
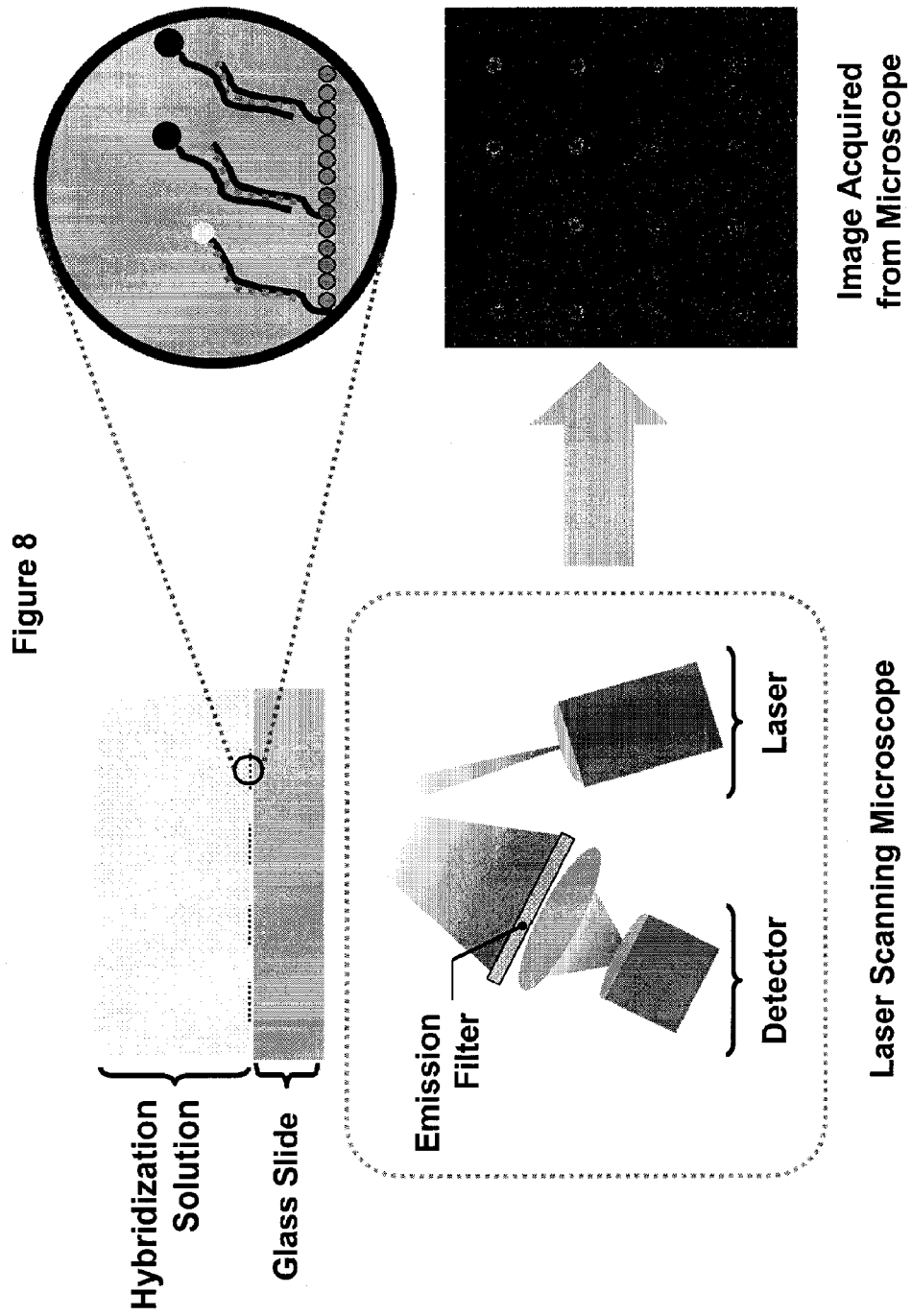
FIG. 8 shows an example of a real-time microarray system An example of a real-time microarray system where binding of BHQ2 quencher-labeled cDNA molecules were detected using a fluorescent laser-scanning microscope.

FIG. 8 shows an example of a real-time microarray system where real-time binding of BHQ2 quencher-labeled cDNA molecules were detected using a fluorescent laser-scanning microscope. The substrate in this example was a transparent glass slides and the probes were 25 bp Cy5-labeled oligonucleotides. The light source (laser) and detector were both located on the back of the substrate.

In some embodiments, the system comprises an instrument that has a detector assembly, and a computing system, where the instrument can accept a sub-assembly. The sub assembly comprises a chamber that will hold the fluid volume and the solid substrate having a surface and a plurality of probes. The sub-assembly can be loaded into the instrument in order to monitor the reaction during the binding event, and after saturation.

In some embodiments, the system comprises: an assay assembly comprising means to engage a microarray and means to perform an assay on a surface of the microarray; and a detector assembly comprising means to detect signals measured at multiple time points from each of a plurality of spots on the microarray during the performance of the assay.

In some embodiments, the means to perform the assay comprise a compartment wherein the surface of the microarray comprises a floor of the compartment and means to deliver reagents and analytes into the compartment. Any method can be used to seal the microarray to the compartment including using adhesives and gaskets to seal the fluid. Any method can be used to deliver reagents and analytes including using syringes, pipettes, tubing, and capillaries.

In some embodiments, the system comprises a means of controlling the temperature. Control of temperature can be important to allow control of binding reaction rates, e.g. by controlling stringency. The temperature can be controlled by controlling the temperature at any place within the system including controlling the temperature of the fluid or the temperature of the solid substrate. Any means can be used for controlling the temperature including resistive heaters, Peltier devices, infrared heaters, fluid or gas flow. The temperatures can be the same or different for solution or substrate or different parts of each. Ideally the temperature is consistently controlled within the binding region. In some embodiments the temperature is controlled to within about 0.01, 0.05, 0.1, 0.5, or 1° C.

In some embodiments the system is capable of changing the temperature during the binding reaction. In some embodiments, the temperature can be rapidly changed during the binding reaction. In some embodiments, the system is capable of changing the temperature at a rate of temperature change corresponding to a change of 1° C. in less than about 0.01 msec, 0.1 msec, 0.5 msec, 1 msec, 5 msec, 10 msec, 50 msec, 100 msec, 0.5 sec, 1 sec, 10 sec, or 60 sec.

In other embodiments the temperature is changed slowly, gradually ramping the temperature over the course of the binding reaction.

One exemplary embodiment of changing the temperature during the binding reaction involves a change in temperature to change the binding stringency and probability. Most bindings in affinity-based biosensors are a strong function of temperature, thus by changing temperature we can alter the stringency and observe the capturing the new capturing process with a new set of capturing probabilities.

In some embodiments, the system is capable of measuring temperature in one or multiple locations in the solution or on the solid substrate. The temperature can be measured by any means including by thermometer, thermocouple, or thermochromic shift.

In some embodiments the system comprises a feedback loop for temp control wherein the measured temperature is used as an input to the system in order to more accurately control temperature.

In some embodiments, the system comprises an apparatus to add or remove material from the fluid volume. In some embodiments, the system can add or remove a liquid from the fluid volume. In some embodiments, the system is capable of adding or removing material from the fluid volume in order to change the: concentration, pH, stringency, ionic strength, or to add or remove a competitive binding agent. In some embodiments, the system is capable of changing the volume of the fluid volume during the reaction.

One exemplary embodiment of adding material to the fluid volume during the binding reaction comprises the addition of incubation buffer. The incubation buffer is the buffer in which the analytes are residing. By adding the incubation buffer, the concentration of analytes in the system will decrease and therefore the binding probability and kinetic of binding will both decrease. Furthermore, if the reaction has already reached equilibrium, the addition of the buffer will cause the system to move another equilibrium state in time.

Another exemplary embodiment of adding material to the fluid volume during the binding reaction is adding a competing binding species. The competing species can be of the same nature of the analyte but in general they are molecules which have affinity to capturing probes. For DNA microarrays for example, the competing species can be synthesized DNA oligo-nucleotides with partially or completely complementary sequence to the capturing probes. In immunoassays, the competing species are antigens.

In some embodiments the system comprises elements to apply an electric potential to the fluid volume to electrically change the stringency of the medium. In some embodiments, the system will provide an electrical stimulus to the capturing region using an electrode structure which is placed in proximity of the capturing region. If the analyte is an electro-active species and/or ion, the electrical stimulus can apply an electrostatic force of the analyte. In certain embodiments, this electrostatic force is adjusted to apply force on the bonds between analyte and capturing probe. If the force is applied to detach the molecule, the affinity of the analyte-probe interaction is reduced and thus the stringency of the bond is evaluated. The electrical stimulus is generally a DC and/or time-varying electrical potentials. Their amplitude can be between 1 mV to 10V, but typically between 10 mV to 100 mV. The frequency of time-varying signal can be between 1 Hz to 1000 MHz, in some embodiments, the frequency of the time-varying signal is between 100 Hz to 100 kHz. The use of electric potential to control stringency is described in U.S. Pat. No. 6,048,690.

In some embodiments the system comprises a computing system for analyzing the detected signals. In some embodiments, the system is capable of transferring time point data sets to the computing system wherein each time point data set corresponds to detected signal at a time point, and the computing system is capable of analyzing the time point data sets, in order to determine a property related to the analyte and probe. The methods of the current invention can, in some cases, generate more data, sometimes significantly more data than for conventional microarrays. Thus a computer system and software that can store and manipulate the data (for instance, images taken at time points) can be essential components of the system. The data can be analyzed in real-time, as the reaction unfolds, or may be stored for later access.

The information corresponding to detected signal at each time point can be single values such as signal amplitude, or can be more complex information, for instance, where each set of signal information corresponds to an image of a region containing signal intensity values at multiple places within an addressable location.

The property related to analyte and/or probe can be, for example, analyte concentration, binding strength, or competitive binding, and cross-hybridization.

In some embodiments the computing system uses the algorithms described above for determining concentration and/or cross-hybridization.

One aspect of the invention is software for use in characterizing binding between analyte and probe. In one embodiment, the software carries out the steps of i) accessing stored images taken at different time points, ii) performing image processing to determine the location of the spots and convert the data to a collection of time series (one for each spot) representing the temporal behavior of the signal intensity for each spot, and iii) for each spot on the array determining whether a reaction has happened (this is often done by comparing with control spots on the array). Optionally, the software can perform the steps of iv) determining whether the reaction at each spot involves the binding of a single analyte or multiple analytes (if, for example, cross-hybridization is occurring), v) estimating the reaction rates using statistical system identification methods. Examples of statistical system identification methods include methods such as Prony's method. In the case that step iv) is used, (multiple bindings per spot), the reaction rate of each binding is determined, and vi) using the reaction rates to estimate the unknown quantity of interest (analyte concentration, binding strength, etc.) using, for example optimal Bayesian methods.

In some embodiments, the system will have software for interfacing with the instrument, for example allowing the user to display information in real-time and allowing for user to interact with the reaction (i.e., add reagents, change the temperature, change the pH, dilution, etc.).

Uses

Where the probe and analyte are nucleic acids, the present invention provides methods of expression monitoring and generic difference screening. The term expression monitoring is used to refer to the determination of levels of expression of particular, typically preselected, genes. The invention allows for many genes, e.g. 10, 100, 1,000, 10,000, 100,000 or more genes to be analyzed at once. Nucleic acid samples are hybridized to the arrays and the resulting hybridization signal as a function of time provides an indication of the level of expression of each gene of interest. In some embodiments, the array has a high degree of probe redundancy (multiple probes per gene) the expression monitoring methods provide accurate measurement and do not require comparison to a reference nucleic acid.

In another embodiment, this invention provides generic difference screening methods, that identify differences in the abundance (concentration) of particular nucleic acids in two or more nucleic acid samples. The generic difference screening methods involve hybridizing two or more nucleic acid samples to the same oligonucleotide array, or to different oligonucleotide arrays having the same oligonucleotide probe composition, and optionally the same oligonucleotide spatial distribution. The resulting hybridizations are then compared allowing determination which nucleic acids differ in abundance (concentration) between the two or more samples.

Where the concentrations of the nucleic acids comprising the samples reflects transcription levels genes in a sample from which the nucleic acids are derived, the generic difference screening methods permit identification of differences in transcription (and by implication in expression) of the nucleic acids comprising the two or more samples. The differentially (e.g., over- or under-) expressed nucleic acids thus identified can be used (e.g., as probes) to determine and/or isolate those genes whose expression levels differs between the two or more samples.

The expression monitoring and difference screening methods of this invention may be used in a wide variety of circumstances including detection of disease, identification of differential gene expression between two samples (e.g., a pathological as compared to a healthy sample), screening for compositions that upregulate or down-regulate the expression of particular genes, and so forth.

EXAMPLES

Example 1

Figure 10:
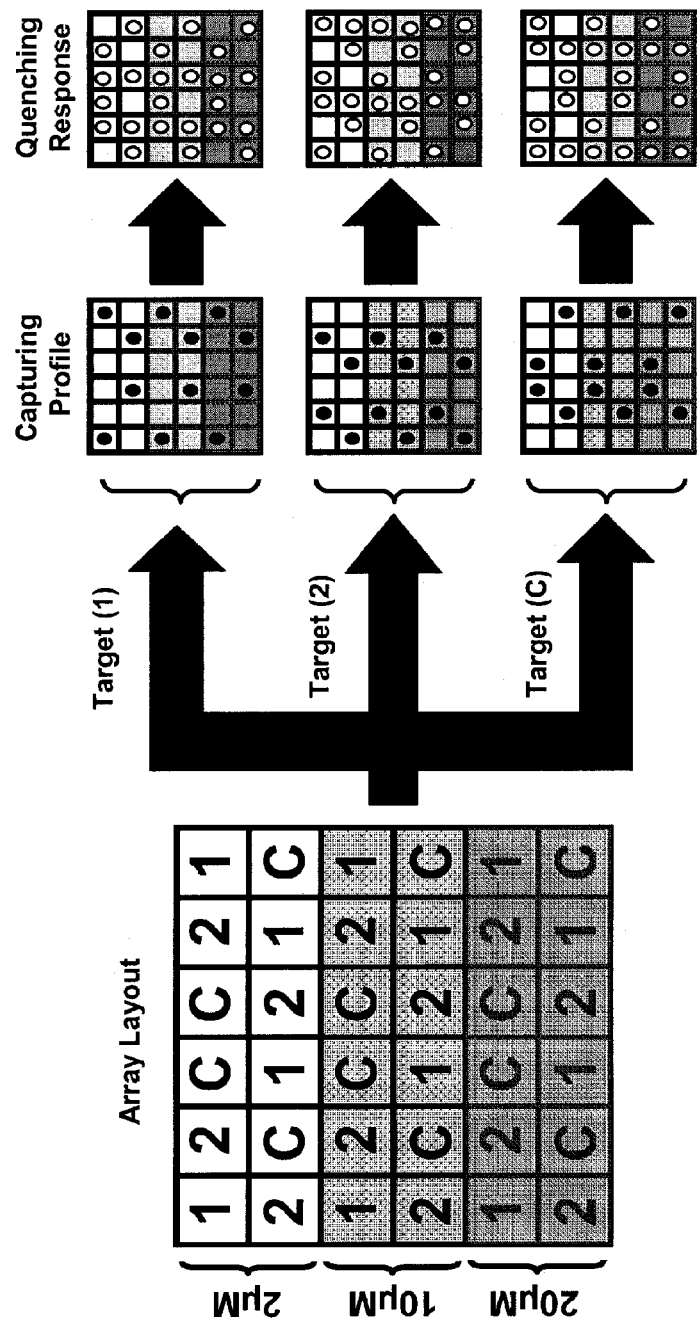
FIG. 10 shows the layout of a 6×6 DNA microarray of the present invention
Figure 12:
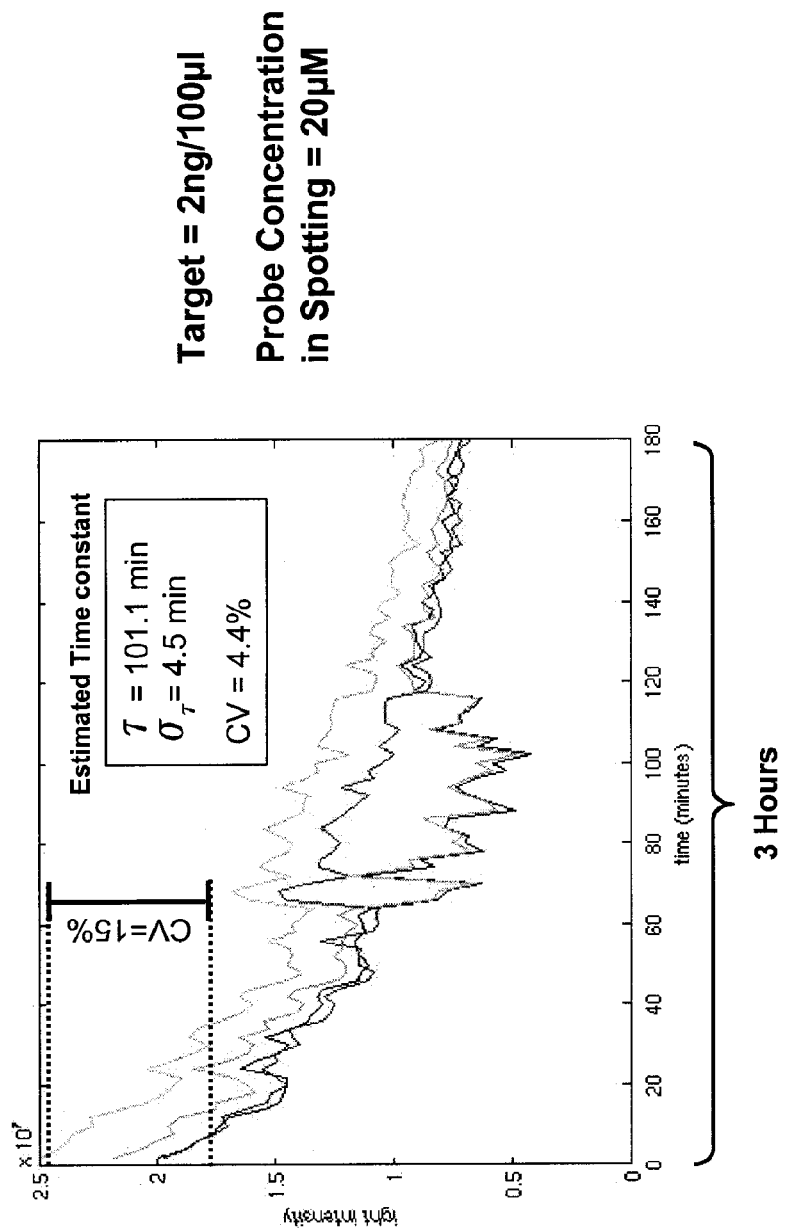
Figure 13:
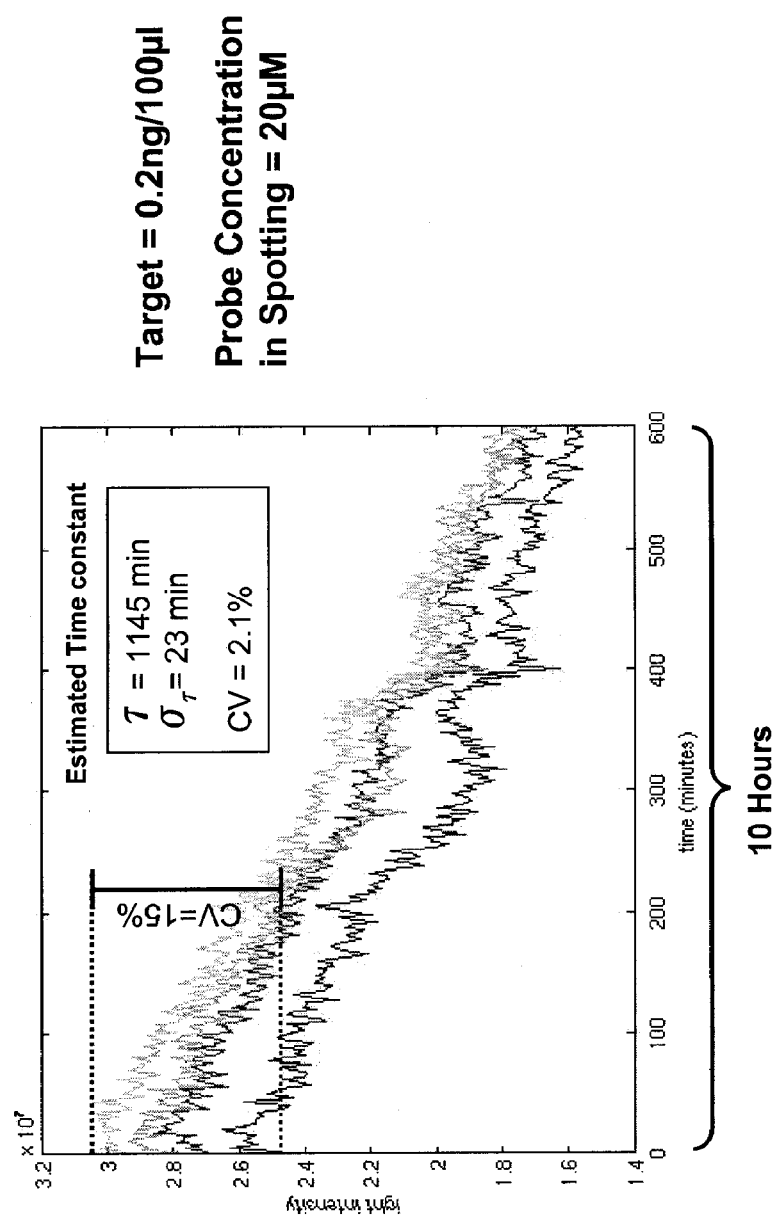
Figure 14:
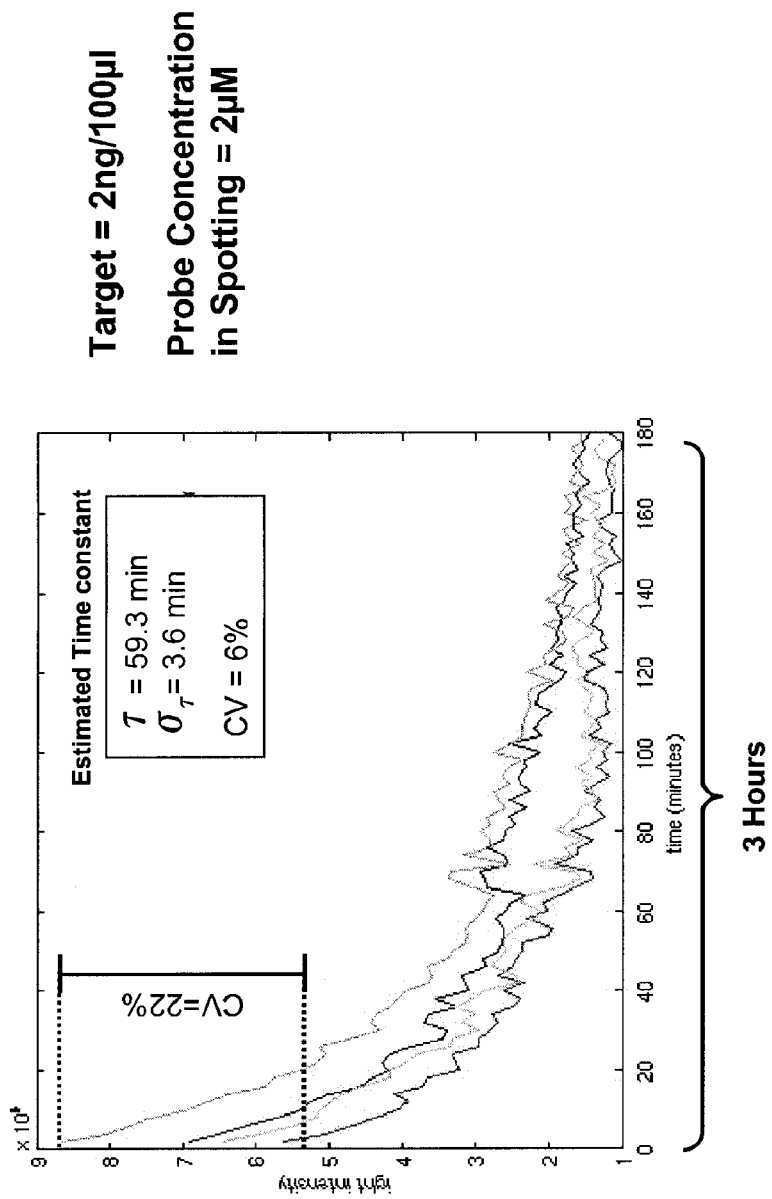
Figure 15:
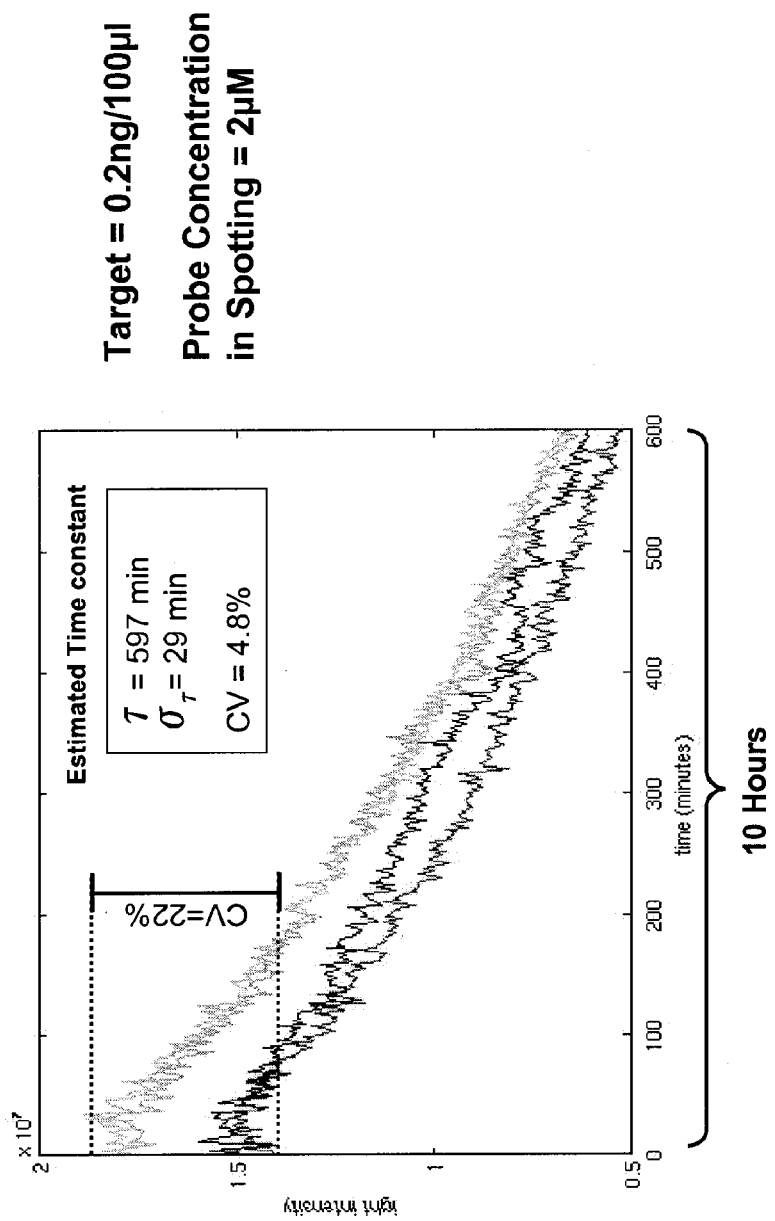

FIG. 10 shows the layout of a 6×6 DNA microarray. Three different DNA probes (1, 2, and Control) with three different concentrations (2 µM, 10 µM, and 20 µM) are spotted and immobilized on the surface as illustrated. The probes contain a single Cy3 fluorescent molecule at the 5' end. The DNA targets in this experiment contain a quencher molecule. The analyte binding in this system results in quenching of fluorescent molecules in certain spots. FIG. 11 shows a few samples of the real-time measurements of the microarray experiment wherein the control targets are added to the system. As illustrated in FIG. 11, the spots are quenched due to analyte binding.

FIGS. 12-15 each show data for 4 different spots with similar oligonucletide capturing probes. The target DNA analyte is introduced in the system at time zero and quenching (reduction of signal) occurs only when binding happens. For FIG. 12, the light intensity coefficient of variation was about 15%, however the estimated time constant rate from real-time measurements had only 4.4% variations. For FIG. 13 the light intensity coefficient of variation was about 15%, however the estimated time constant rate from real-time measurements had only 2.1% variations. For FIG. 14 the light intensity coefficient of variation was about 22%, however the estimated time constant rate from real-time measurements had only 6% variations. For FIG. 15 the light intensity coefficient of variation was about 22%, however the estimated time constant rate from real-time measurements had only a 4.8% variation.

Figure 16:
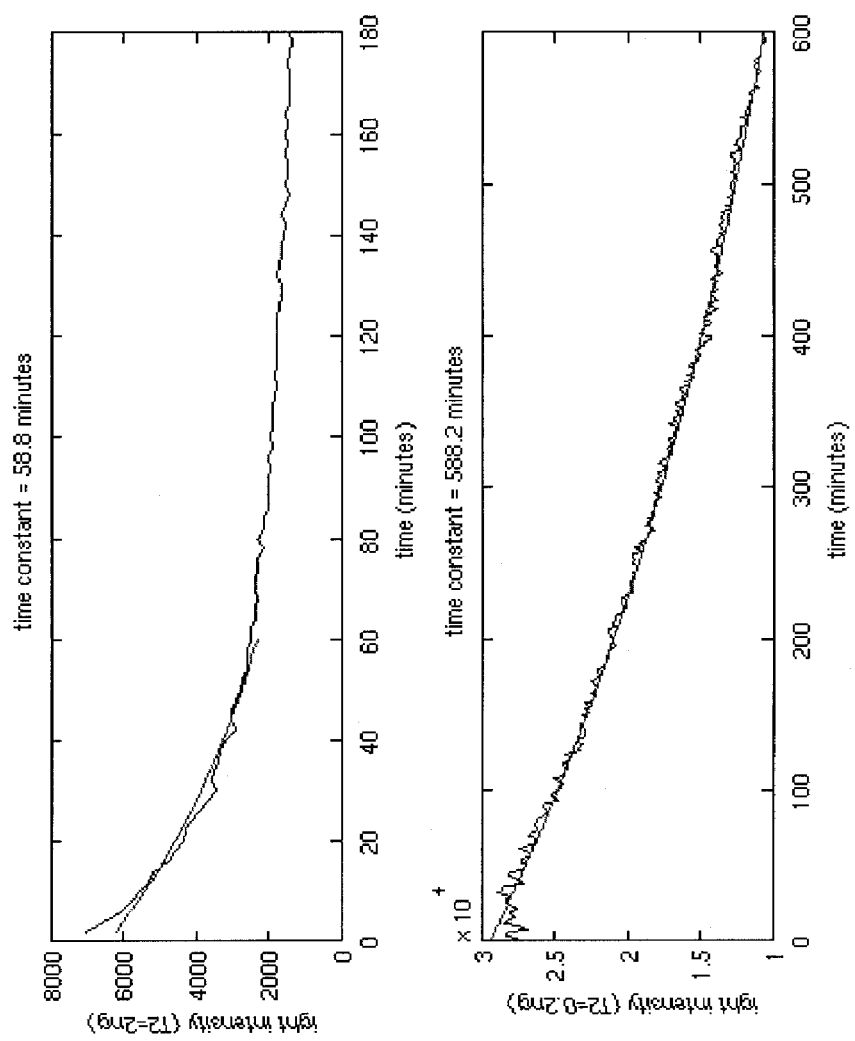
FIG. 16 shows the signals measured during two real-time experiments wherein a target analyte (target 2) is applied to the microarray, at 2 ng and at 0.2 ng.

In FIG. 16, the signals measured during two real-time experiments wherein target 2 is applied to the microarray, first at 2 ng and then at 0.2 ng, are shown. The measured light intensities at the corresponding probe spots decay over time as the targets to the probes bind and the quenchers come in close proximity to the fluorescent labels attached to the end of the probes. The rate of the decay, which can be estimated by a curve fitting technique, is proportional to the amount of the target present. The time constant of the measured process is defined as the inverse of the rate of decay. The ratio of the time constants of the two processes is 10, which is precisely the ratio of the amounts of targets applied in the two experiments.

Example 2

This example provides a derivation of an algorithm, and the use of the algorithm to determine analyte concentration from a real-time binding data. The derivation proceeds as follows:

Assume that the hybridization process starts at $t=0$, and consider discrete time intervals of the length $\Delta t$. Consider the change in the number of bound target molecules during the time interval $(i\Delta t, (i+1)\Delta t)$. We can write $$n_b(i+1) - n_b(i) = [n_t - n_b(i)]p^b(i)\Delta t - n_b(i)p_r(i)\Delta t,$$

where $n_t$ denotes the total number of target molecules, $n_b(i)$ and $n_b(i+1)$ are the numbers of bound target molecules at $t=i\Delta t$ and $t=(i+1)\Delta t$, respectively, and where $p_b(i)$ and $p_r(i)$ denote the probabilities of a target molecule binding to and releasing from a capturing probe during the $i^{th}$ time interval, respectively. Hence, $$\frac{n_b(i+1) - n_b(i)}{\Delta t} = [n_t - n_b(i)]p_b(i) - n_b(i)p_r(i). \quad (1)$$

It is reasonable to assume that the probability of the target release does not change between time intervals, i.e., $p_r(i) = p_r$, for all $i$. On the other hand, the probability of forming a target-probe pair depends on the availability of the probes on the surface of the array. If we denote the number of probes in a spot by $n_p$, then we can model this probability as $$p_b(i) = \left(1 - \frac{n_b(i)}{n_p}\right) \cdot p_b = \frac{n_p - n_b(i)}{n_p} p_b, \quad (2)$$

where $p_b$ denotes the probability of forming a target-probe pair assuming an unlimited abundance of probes.

By combining (1) and (2) and letting $\Delta t \to 0$, we arrive to $$\frac{dn_b}{dt} = (n_t - n_b)\frac{n_p - n_b}{n_p} p_p - n_b p_r \quad (3)$$

$$= n_t p_b - \left[\left(1 - \frac{n_t}{n_p}\right)p_b + p_r\right]n_b + \frac{p_b}{n_p}n_b^2$$

Note that in (3), only $n_b = n_b(t)$, while all other quantities are constant parameters, albeit unknown. Before proceeding any further, we will find it useful to denote $$\alpha = \left(1 + \frac{n_t}{n_p}\right)p_b + p_r, \beta = n_t p_b, \gamma = \frac{p_b}{n_p}. \quad (4)$$

Clearly, from (4), $$p_b = \frac{\beta}{n_t}, n_p = \frac{p_b}{\gamma}, p_r = \alpha - \left(1 + \frac{n_t}{n_p}\right)p_b.$$

Using (4), we can write (3) as $$\frac{dn_b}{dt} = \beta - \alpha n_b + \gamma n_b^2 = \gamma(n_b - \lambda_1)(n_b - \lambda_2), \quad (5)$$

where $\lambda_1$ and $\lambda_2$ are introduced for convenience and denote the roots of $\beta - \alpha n_b + \gamma n_b^2 = 0$.

Note that $\gamma = \beta(\lambda_1 \lambda_2)$. The solution to (5) is found as $$n_b(t) = \lambda_1 + \frac{\lambda_1(\lambda_1 - \lambda_2)}{\lambda_2 e^{\beta\left(\frac{1}{\lambda_1} - \frac{1}{\lambda_2}\right)t} - \lambda_1}.$$

We should point out that (3) describes the change in the amount of target molecules, $n_b$, captured by the probes in a single probe spot of the microarray. Similar equations, possibly with different values of the parameters $n_p$, $n_t$, $p_b$, and $p_r$, hold for other spots and other targets.

Estimating Parameters of the Model

The following is an outline of a procedure for estimation of the parameters. Ultimately, by observing the hybridization process, we would like to obtain $n_t$, $n_p$, $p_b$, and $p_r$. However, we do not always have direct access to $n_b(t)$ in (6), but rather to $y_b(t) = k n_b(t)$, where k denotes a transduction coefficient. In particular, we observe $$y_b(t) = \lambda_1^* + \frac{\lambda_1^*(\lambda_1^* - \lambda_2^*)}{\lambda_2^* e^{\beta\left(\frac{1}{\lambda_1^*} - \frac{1}{\lambda_2^*}\right)t} - \lambda_1^*}, \quad (7)$$

where $\lambda_1^* = k\lambda_1$, $\lambda_2^* = k\lambda_2$, and $\beta^* = k\beta$.

For convenience, we also introduce $$\gamma^* = \frac{\beta^*}{\lambda_1^* \lambda_2^*} = \frac{\gamma}{k}, \alpha^* = \gamma^*(\lambda_1^* + \lambda_2^*) = \alpha. \quad (8)$$

From (5), it follows that $$\beta^* = \left.\frac{dy_b}{dt}\right|_{t=0}. \quad (9)$$

Assume, without a loss of generality, that $\lambda 1^*$ is the smaller and $\lambda_2^*$ the larger of the two, i.e., $\lambda_1^* = \min(\lambda_1, \lambda_2)$, and $\lambda_2^* = \max(\lambda_1, \lambda_2)$. From (7), we find the steady-state of $y_b(t)$, $\lambda_1^* = \lim y_b(t), t \to \infty$. (10)

So, from (9) and (10) we can determine $\beta^*$ and $\lambda 1^*$, two out of the three parameters in (7). To find the remaining one, $\lambda_2^*$, one needs to fit the curve (7) to the experimental data.

Having determined $\beta^*$, $\lambda 1^*$, and $\lambda_2'$, we use (8) to obtain $\alpha^*$ and $\gamma^*$. Then, we should use (4) to obtain $p_b$, $p_r$, $n_p$, and $n_t$ from $\alpha^*$, $\beta^*$, and $\gamma^*$. However, (4) gives us only 3 equations while there are 4 unknowns that need to be determined. Therefore, we need at least 2 different experiments to find all of the desired parameters. Assume that the arrays and the conditions in the two experiments are the same except for the target amounts applied. Denote the target amounts by $n_t$, and $n_t$; on the other hand, $p_b$ and $p_r$ remain the same in the two experiments. Let the first experiment yield $\alpha_1^*$, $\beta_1^*$, and $\gamma_1^*$, and the second one yield $\alpha_2^*$, $\beta_2^*$, and $\gamma_2^*$ (we note that $\gamma_1 = \gamma_2^*$). Then it can be shown that $$p_b = \frac{\beta_1^* \gamma_1^* - \beta_2^* \gamma_2^*}{\alpha_1^* - \alpha_2^*}, \quad (11)$$

and $$p_r = \alpha_1^* - p_b - \frac{\beta_1^* \gamma_1^*}{p_b}. \quad (12)$$

Moreover, $$n_p = \frac{p_b}{k\gamma_1^*}, \quad (13)$$

and $$n_{t1} = \frac{\beta_1^* \gamma_1^*}{p_b^2} n_p, n_{t2} = \frac{\beta_2^* \gamma_2^*}{p_b^2} n_p. \quad (14)$$

We note that quantities (13)-(14) are known within the transduction coefficient k, where $k = y_b(0) n_p$. To find k and thus unambiguously quantify $n_p$, $n_{t1}$, and $n_{t2}$, we need to perform a calibration experiment (i.e., an experiment with a known amount of targets $n_t$).

Experimental Example

Figure 17:
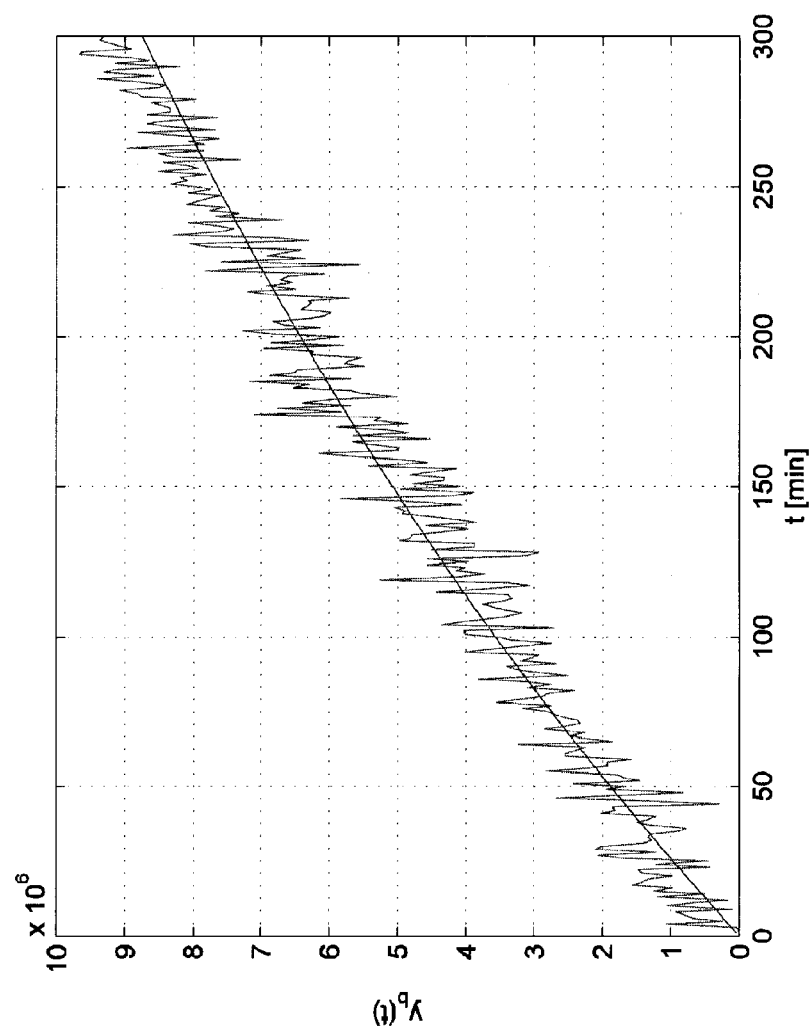
FIG. 17 shows the signal versus time measured in a real-time oligonucleotide array, and the fit of the data to an algorithm, where 80 ng/50 µl of the target is applied to the array.
Figure 18:
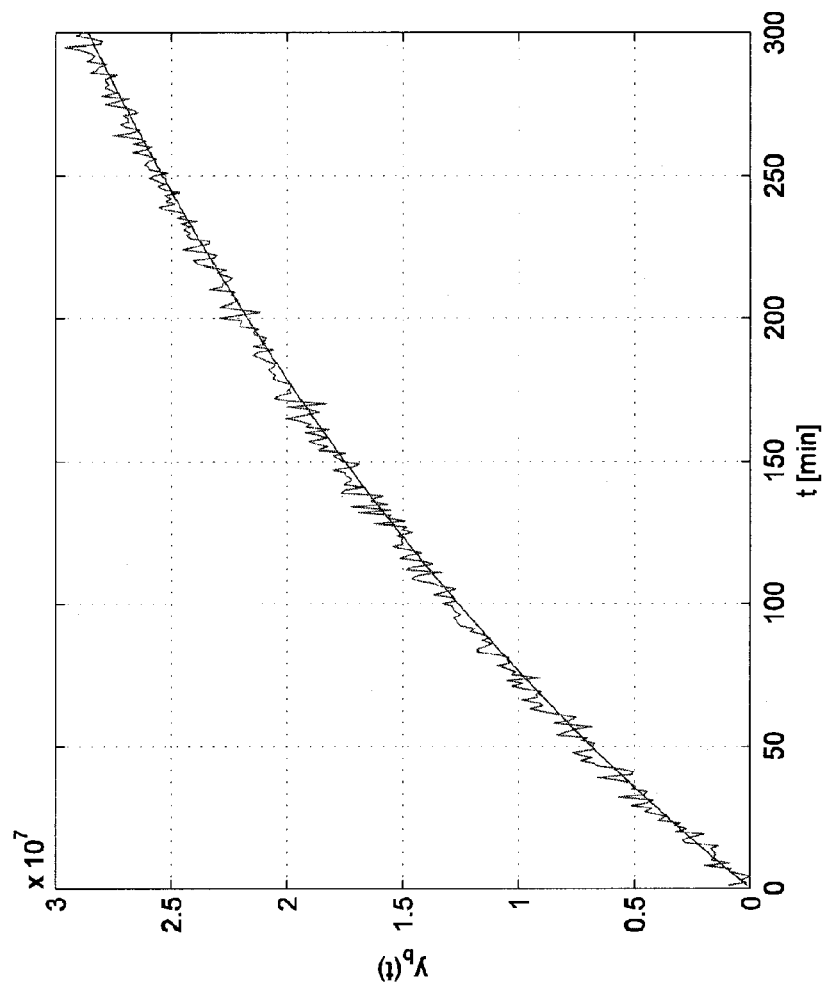
FIG. 18 shows the signal measured in a real-time oligonucleotide array, and the fit of the data to an algorithm, where 16 ng/50 µl of the target is applied to the array.

Here we describe the experiments designed to test the validity of the proposed model and demonstrate the parameter estimation procedure. To this end, two DNA microarray experiments are performed. The custom 8-by-9 arrays contain 25mer probes printed in 3 different probe densities. The targets are Ambion mRNA Spikes, applied to the arrays with different concentrations. The concentrations used in the two experiments are 80 ng/50 µl and 16 ng/50 µl. The signal measured in the first experiment, where 80 ng of the target is applied to the array, is shown in FIG. 17. The smooth line shown in the same figure represents the fit obtained according to (7). In the second experiment, 16 ng of the target is applied to the array. The measured signal, and the corresponding fit obtained according to (7), are both shown in FIG. 18.

Applying (11)-(14), we obtain $p_b = 1.9 \times 10^{-1}, p_r = 2.99 \times 10^{-5}$.

Furthermore, we find that $n_{t2}/n_{t2} = \beta_1^* \beta_2^* = 3.75$ (15)

Note that the above ratio is relatively close to its true value, 80/16 = 5. Finally, assuming that one of the experiments is used for calibration, we find that the value of the transduction coefficient is $k = 4.1 \times 10^{-4}$, and that the number of probe molecules in the observed probe spots is $n_p = 1.6 \times 10^{-11}$.

Example 3

This example shows how the methods and systems of the present invention can be used for measurement of gene expression. Real-time microarray technology can measure, for example, expression level differences for different cell types or tissues, distinct developmental stages, cancerous versus normal cells or tissues, treated versus untreated cells or tissues, mutant versus wild-type cells, tissues or organisms.

The gene expression profiles of inflorescences of the *Arabidopsis thaliana* floral homeotic mutants apetala1, apetala2, apetala3, pistillata, and agamous can be compared with that of wild-type plants. By combining the data sets from the individual mutant/wild type comparisons, it is possible to identify a large number of genes that are, within flowers, predicted to be specifically or at least predominantly expressed in one type of floral organ. For each sample, floral buds from approximately 50 plants are collected, and RNA is isolated from 100 mg of tissue with the RNeasy RNA Isolation Kit (Qiagen). To prepare labeled target material from those samples, an in vitro transcription amplification method followed by aminoallyl-UTP-mediated labeling is used. In brief, first and second strand cDNA is synthesized from 3 μg of total RNA using a polyA-primer with a T7 promoter sequence. Then in vitro transcription is performed using the Megascript T7 kit (Ambion), in the presence of aminoallyl-UTP and of a reduced amount of UTP, to incorporate the modified aaUTP into the aRNA during the transcription process. Finally, dye molecules (Cy3 Mono-Reactive Dye, Cy5 Mono-Reactive Dye, Amersham) are coupled to the amplified RNA and the dye-labeled RNA is fragmented before hybridization. These and similar protocols are well established in the microarray field and are well known to those skilled in the art, and commercial kits are available for cDNA synthesis, in vitro transcription amplification, and amino-allyl labeling, such as the Amino Allyl MessageAmp™ II aRNA Amplification Kit, from Ambion. Aminoallyl UTP contains a reactive primary amino group on the C5 position of uracil that can be chemically coupled to N-hydroxysuccinimidyl ester-derivatized reactive dyes (NHS ester dyes), in a simple efficient reaction.

Amine-reactive quenchers are commercially available, for example QSY® 9 carboxylic acid, succinimidyl ester, from Invitrogen. The real-time microarray technology is used with minimal modifications to the sample preparation and labeling procedures: namely, with the simple substitution of the QSY-9 ester for the Cy-dye ester. In this case, total RNA samples are prepared as described above. The purified total RNA is then amplified using the Amino Allyl MessageAmp™ II aRNA Amplification Kit, from Ambion, and the resulting aRNA is labeled with QSY9. This labeled RNA population is then used in hybridization with *Arabidopsis* real-time microarrays. Such arrays consist of an arranged collection of probes that correspond to all (or a subset of) the genes in the *Arabidopsis* genome. The oligonucleotide probes are labeled with a fluorescent moiety (such as Cy3) and printed by contact deposition onto CodeLink slides (GE Healthcare), which are processed and blocked after printing following manufacturer's instructions.

Example 4

This example relates to using an algorithm to measure cross-hybridization. A variety of different techniques to recover the signal, including, but not limited to, total least squares, ESPRIT, and Prony's method, (see Dowling et. al. IEEE Trans. on Antennas and Propag., vol. 42, no. 5, 1994 and van der Veen et al. Proc. of the IEEE, 81(9):1277-1308, 1993).

Figure 19:
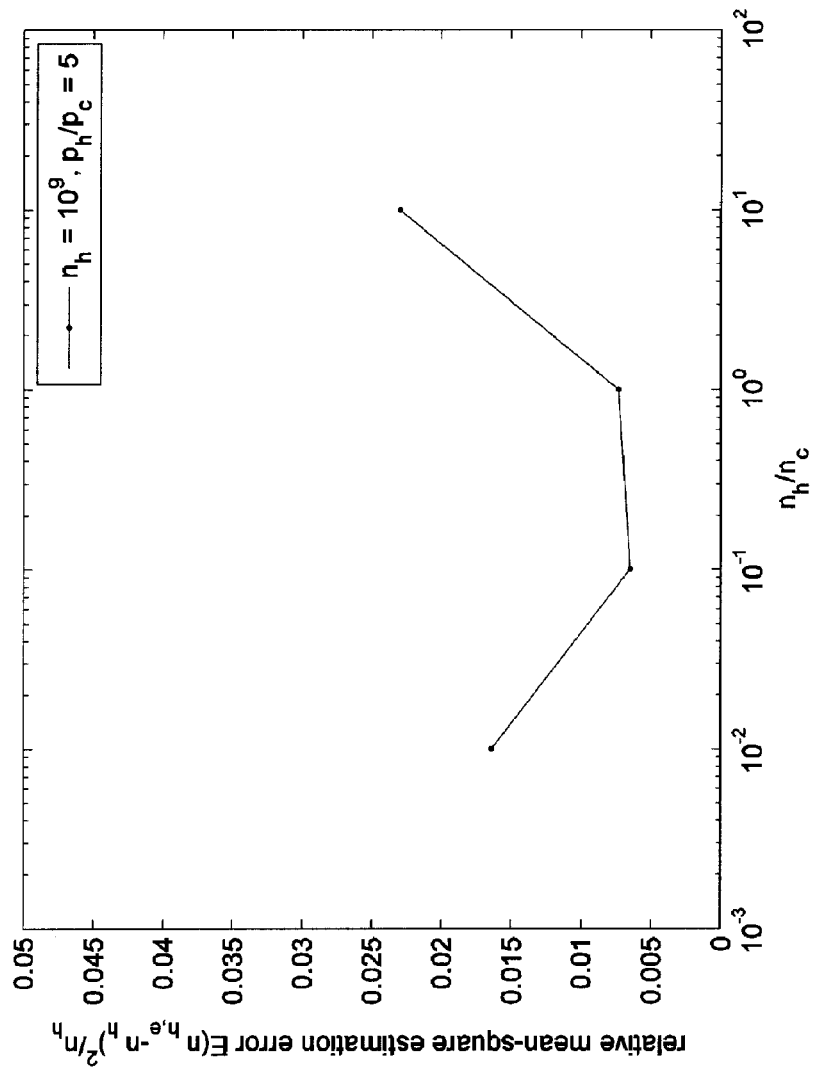
FIG. 19 shows the results of a simulation indicating the potential of suppression of cross-hybridization over 3 orders of magnitude.

In this example we study the performance of one such algorithm in simulation and illustrate the results in FIG. 19. In particular, we consider the so-called total least squares (TLS) algorithm in the situation where two target analytes bind to the same probe spot—one due to hybridization, and the other due to cross-hybridization. Parameters of the system (probabilities of hybridization, cross-hybridization, release, etc.) are chosen so as to mimic realistic experimental scenarios. The probability of hybridization is assumed to be 5 times greater than the probability of cross-hybridization (i.e., $p_h/p_c=5$). The number of hybridizing target is $n_h=10^9\$$, while the number of cross-hybridizing molecules is varied. In FIG. 19, we plot the relative mean-square error of estimating $n_h$ (averaged over many realizations of noise) as a function of the ratio $n_h/n_c$. The simulation results indicate potentially successful suppression of cross-hybridization over 3 orders of magnitude of $n_h/n_c$.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of measuring at least one parameter of a binding reaction of an analyte with a probe on a microarray, comprising the steps of:
   contacting a fluid volume comprising an initial concentration C of at least one analyte that is labeled with a quencher with a solid substrate comprising a number Po of unbound molecules of at least one probe that has been labeled with a donor and affixed thereto at a probe spot, said at least one probe and said at least one analyte configured to bind together, wherein the at least one analyte is not labeled with a metal cluster;
   measuring kinetically in real-time a plural number of values for the number P(t) of unbound molecules of said probe at time t, during a time interval when said reaction of said at least one probe and said at least one analyte is occurring, wherein said reaction is not competitive;
   determining by using said measured plural number of values P(t) fitted to an exponential curve at least one parameter descriptive of a binding reaction of said at least one probe and said at least one analyte; and
   performing a selected one of storing, manipulating and displaying to a user data comprising said at least one parameter,
   wherein said contacting and measuring are performed in the absence of a washing step.

2. The method of claim 1, wherein said at least one parameter descriptive of a binding reaction of said at least one probe and said at least one analyte comprises a selected one of the following parameters:
   a forward binding reaction rate;
   a backward binding reaction rate;
   C which is an original analyte quantity in said fluid volume;
   $C-(P_0-P(t))$ which is an available analyte density at time t;
   t which is a time constant;
   $P_\infty$ which is a steady-state value of P(t);
   n(t) which is a number of analytes in said fluid volume that are specific to said probe molecule;
   $P_{near}$ which is a probability that said analyte is in close proximity to said probe molecule;
   $P_h$ which is a probability that, in a unit interval of time, said analyte binds to said probe once said analyte is near;
   $P_r$ which is a probability that, in a unit interval of time, said analyte bound to said probe molecule is released;
   N which is a total number of analyte molecules;

q(t) which is a number of unbound molecules of said at least one analyte as a function of time;
a reaction rate between said analyte and said probe; and
a cross-hybridization parameter.

3. The method of claim 1, wherein said measuring step occurs before said reaction reaches an equilibrium.

4. The method of claim 1, wherein said measuring step uses an optical signal.

5. The method of claim 4, wherein said optical signal is a selected one of a fluorescence signal, a luminescence signal, and an absorption signal.

6. The method of claim 4, wherein said optical signal involves fluorescence resonance energy transfer.

7. The method of claim 1, further comprising the step of determining how many analyte molecules are bound to said probe spot.

8. The method of claim 1, wherein said fluid volume further contains a plurality of different analytes and said solid substrate further comprises a plurality of different probes.

9. The method of claim 1, wherein said measuring a plural number of values for the number P(t) occurs in a time interval of one millisecond or less.

10. The method of claim 1, wherein said donor is a fluorophore.

* * * * *